United States Patent [19]
Johnson et al.

[11] Patent Number: 5,767,078
[45] Date of Patent: Jun. 16, 1998

[54] AGONIST PEPTIDE DIMERS

[76] Inventors: Dana L. Johnson, 1343 Lonely Cottage Rd., Upper Black Eddy, Pa. 18972; Robert A. Zivin, 6 Glenbrook Ct., Lawrenceville, N.J. 08648

[21] Appl. No.: 484,135

[22] Filed: Jun. 7, 1995

[51] Int. Cl.$^6$ .................... A61K 38/00; C07K 2/00; C07K 5/00; C07K 7/00
[52] U.S. Cl. .................. 514/12; 514/13; 514/14; 514/15; 530/300; 530/324; 530/326; 530/345
[58] Field of Search .................. 514/12, 13, 14, 514/15; 580/300, 324, 326, 345

[56] References Cited

FOREIGN PATENT DOCUMENTS

WO 90/08822  8/1990  WIPO .

OTHER PUBLICATIONS

Vedovato et al. (1984) *Acta. Haematol.* 71:211–213.
Vichinsky et al. (1984) *J. Pediatric* 105:15–21.
Cotes et al. (1983) *Brit. J. Ostet. Gyneacol.* 90:304–311.
Haga et al. (1983) *Acta Pediatr. Scand.* 72:827–831.
Claus-Walker (1983) *Acta Pediatr. Scand.* 72:827–831.
Dunn et al. (1984) *Eur. J. Appl. Physiol.* 52:178–182.
Miller et al. (1982) *Brit. J. Haematol.* 52:545–590.
Upda et al. (1984) *J. Lab. Clin. Med.* 103:574–588.
Dainiak et al. (1983) *Cancer* 5:1101–1106.
Eschbach et al. (1987) *N. Engl. J. Med.* 316:73–78.
Krantz and Goldwasser (1984) *Proc. Natl. Acad. Sci. USA*, 81:7574–7578.
Branch et al. (1987) *Blood* 69:1782–1785.
Mayeux et al. (1987) *FEBS Letters* 211:22–223.
Mufson and Gesner (1987) *Blood* 69:1485–1490.
Sakaguchi et al. (1987) *Biochem. Biophys. Res. Commun.* 146:7–12.
Sawyer et al. (1987) *Proc. Natl. Acad. Sci. USA*, 84:3690–3694.
Sawyer et al. (1987) *J. Biol. Chem.* 262:5554–5562.
Todokoro et al. (1988) *Proc. Natl. Acad. Sci. USA*, 84:4126–4130.
Amagnosou et al. (1990) *Proc. Natl. Acad. Sci. USA*, 87:5978–5982.
Konishi et al. (1993) *Brain Res.* 609:29–35.
Heldin, et al., Ligand–Induced Dimerization of Growth Factor Receptors: Variations on the Theme. Cytokine Growth Factor Rev., vol. 7 No. 1, pp. 3–10, 1996.
Dorland's Illustrated Medical Dictionary, 27th Edition, pp. 1432–1433, 1988.

*Primary Examiner*—Cecilia J. Tsang
*Assistant Examiner*—Jennifer Harle
*Attorney, Agent, or Firm*—John W. Wallen, III

[57] ABSTRACT

The present invention is directed to the dimerization of agonists and antagonists of cell surface receptors and particularly to peptide dimers which behave as cell surface receptor agonists in their dimeric form. Such receptors belong to the dimerization-mediated activation class often observed among receptors for growth and differentiation factors. The agonists of this class of receptors is understood to effect dimerization of the receptor and thus signal initiation. The present invention exemplifies dimers of erythropoietin (EPO) agonists and antagonists comprising a core amino acid sequence of $X_3X_4X_5GPX_6TWX_7X_8$ (SEQ ID NO: 1) wherein each amino acid is indicated by standard one letter abbreviation; $X_3$ can be C, A, α-amino-γ-bromobutyric acid or Hoc; $X_4$ can be R, H, L or W; $X_5$ can be M, F, or I; $X_6$ is independently selected from any one of the 20 genetically coded L-amino acids or the stereoisomeric D-amino acids; $X_7$ can be D, E, I, L or V; and $X_8$ can be C, A, α-amino-γ-bromobutyric acid or Hoc, provided that either $X_3$ or $X_8$ is C or Hoc.

9 Claims, 17 Drawing Sheets

FIG. 2 PREPARATIVE REVERSE PHASE ANALYSIS OF PEG-RWJ 61233 DIMER

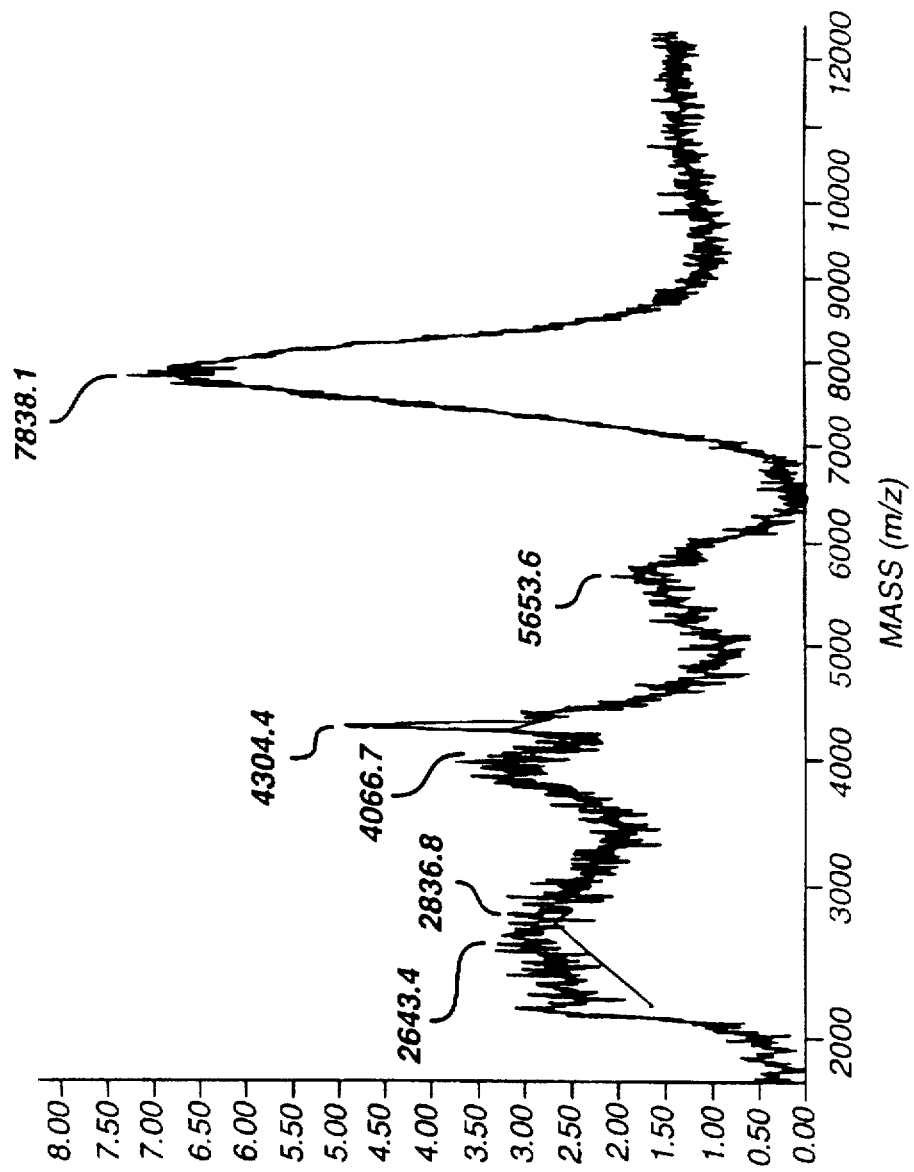
FIG. 3 (B)   SAP2/RWJ 61233, NEUTRALIZED MATRIX

A. NON REDUCING 10-20% SDS-PAGE, B. REDUCING 10-20% SDS-PAGE

| LANE | MWM | EBP | RWJ | 61233 | | 61279 | | 61177 | | 61596 | | |
|---|---|---|---|---|---|---|---|---|---|---|---|---|
| | 1 | 2 | | 3 | 4 | 5 | 6 | 7 | 8 | 9 | 10 | 11 |
| PEPTIDE($\mu M$) | | | | 400 | 400 | 400 | 400 | 400 | 400 | 400 | 400 | --- |
| EBP ($\mu M$) | | | | 22 | 22 | 22 | 22 | 22 | 22 | 22 | 22 | 22 |
| | | | | 0 | 1.1 | 0 | 1.1 | 0 | 1.1 | 0 | 1.1 |
| DPDPB (mM) | | | | 1.1 | | | | | | | | |

| RWJ No. | SEQUENCE | $IC_{50}(\mu M)$ | EPO-$ED_{50}$ ($\mu M$) |
|---|---|---|---|
| 61233+ | GGTYSCHFGPLTWVCKPQGG | 5 | 0.1 |
| 61279 | YSCHFGPLTWVCK | 70 | 3 |
| 61177 | SCHFGPLTWVCK | 90 | IA |
| 61596 | GGTYSCHFGPLTWVCKPQ | 8 | 0.08 |

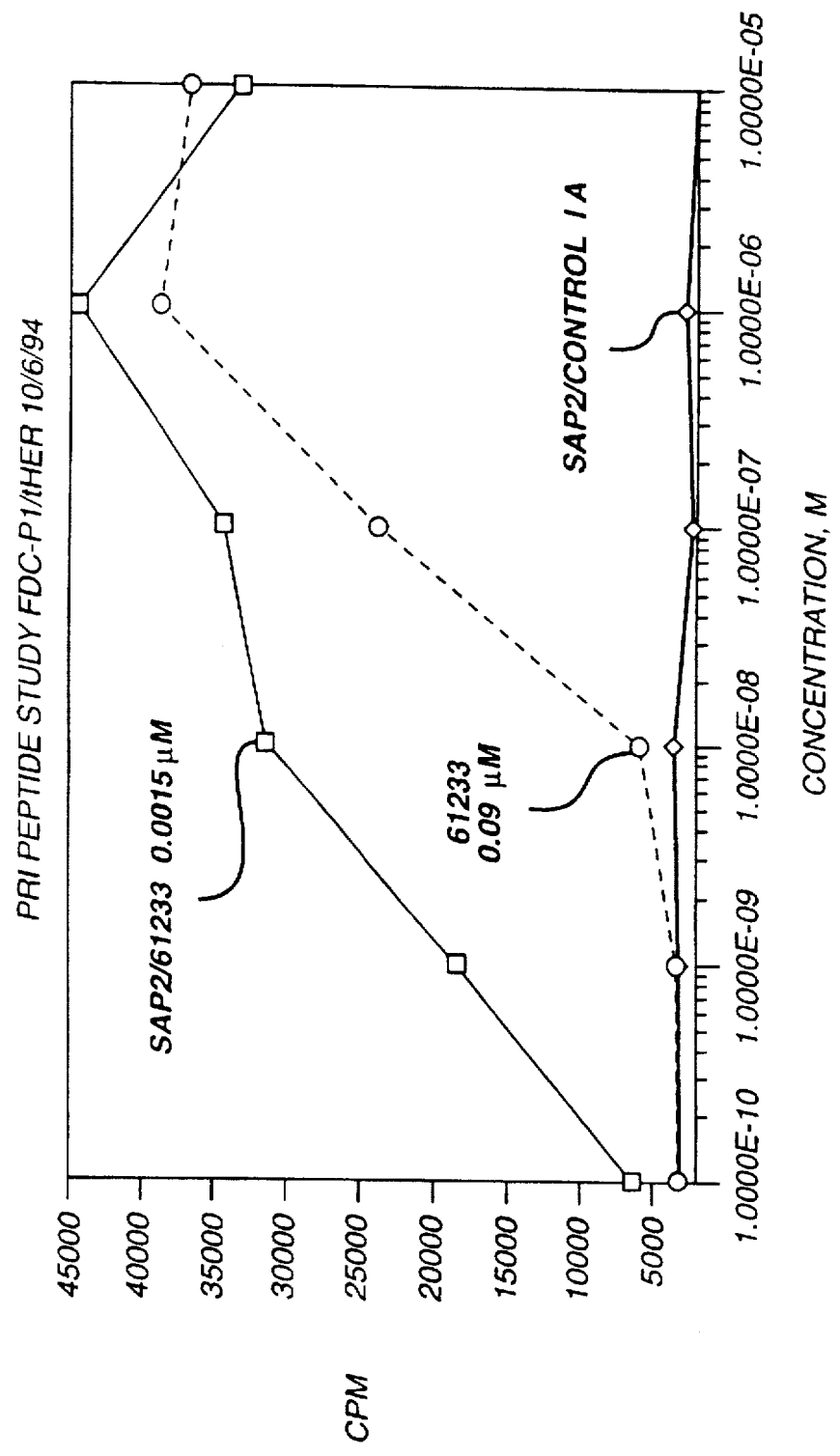
FIG. 6 (B) CELL PROLIFERATION, HUMAN EPOR

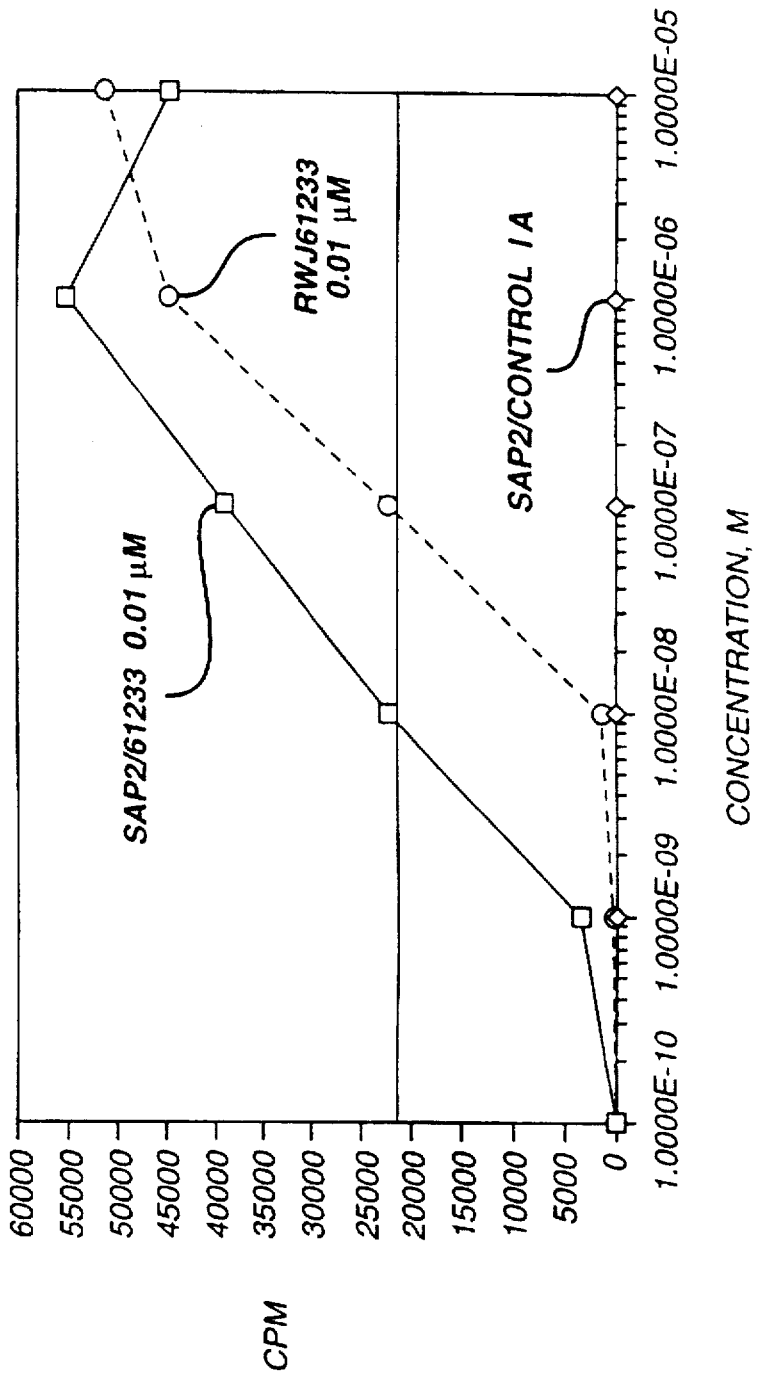

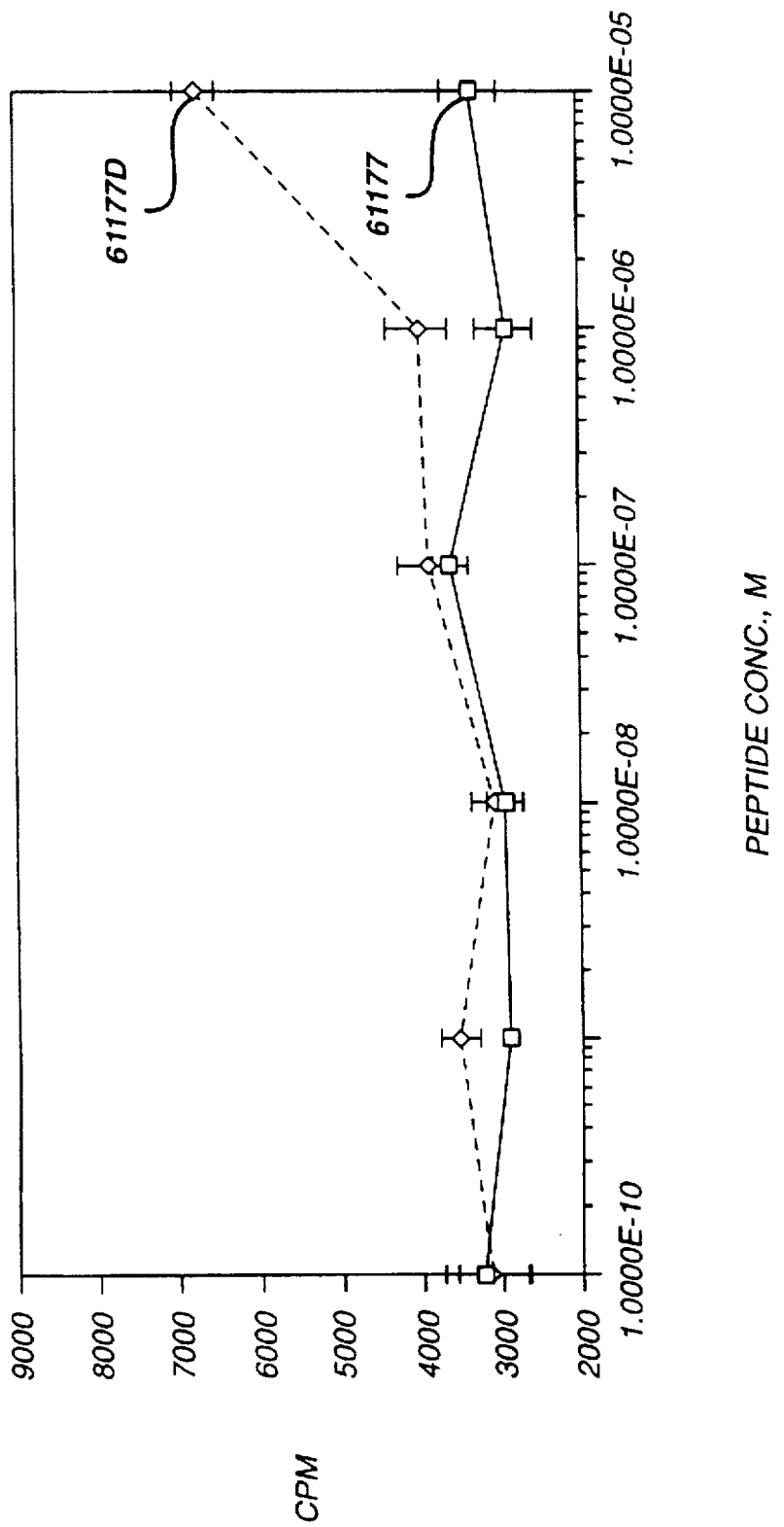

FIG. 9 (A)

| | |
|---|---|
| Ac-GGTYSCHFGPLTWVCKPQGG | SEQ ID NO: 20 |
| GGTYRCSMGPMTWVCLPMGG | SEQ ID NO: 21 |
| GGMYSCRMGPMTWVCGPSGG | SEQ ID NO: 22 |
| GGWAWCRMGPITWVCSAHGG | SEQ ID NO: 23 |
| GGMYSCRMGPNTWVCIPYGG | SEQ ID NO: 24 |
| GGEYKCYMGPITWVCKPEGG | SEQ ID NO: 25 |
| GGDYTCPMGPMTWICTATGG | SEQ ID NO: 26 |
| GGNYLCRFGPGTWDCTGFRG | SEQ ID NO: 27 |
| GGNYVCRMGPITWICTPAGG | SEQ ID NO: 28 |
| GGKDVCRMGPITWDCRSTGG | SEQ ID NO: 29 |
| GGSYLCRMGPTTWLCTAQRGGGN | SEQ ID NO: 30 |
| GGNYLCPMGPATWVCGRMGG | SEQ ID NO: 31 |
| GGEYKCRMGPLTWVCQYAGG | SEQ ID NO: 32 |
| GGDYTCRMGPMTWICTATRG | SEQ ID NO: 33 |
| GGVYVCRMGPLTWECTASGG | SEQ ID NO: 34 |
| GGEYSCRMGPMTWVCSPTGG | SEQ ID NO: 35 |
| GGEYLCRMGPITWVCERYGG | SEQ ID NO: 36 |
| GGNYICRMGPMTWVCTAHGG | SEQ ID NO: 37 |
| GGDYLCRMGPATWVCGRMGG | SEQ ID NO: 38 |
| GGLYLCRFGPVTWDCGYKGG | SEQ ID NO: 39 |
| GGLYSCRMGPITWVCTKAGG | SEQ ID NO: 40 |
| GGGYHCRMGPMTWVCRPVGG | SEQ ID NO: 41 |
| GGTYSCHFGPLTWVCKPQGG | SEQ ID NO: 42 |
| GGIYKCLMGPLTWVCTPDGG | SEQ ID NO: 43 |
| GGLYSCLMGPITWLCKPKGG | SEQ ID NO: 44 |
| GGDYHCRMGPLTWVCKPLGG | SEQ ID NO: 45 |
| GGDYSCRMGPTTWVCTPPGG | SEQ ID NO: 46 |
| GGDYWCRMGPSTWECNAHGG | SEQ ID NO: 47 |
| GGKYLCSFGPITWVCARYGG | SEQ ID NO: 48 |
| GGLYKCRLGPITWVCSPLGG | SEQ ID NO: 49 |
| GGSYTCRFGPETWVCRPNGG | SEQ ID NO: 50 |
| GGSYSCRMGPITWVCKPGGG | SEQ ID NO: 51 |
| GGSYTCRMGPITWVCLPAGG | SEQ ID NO: 52 |
| GGLYECRMGPMTWVCRPGGG | SEQ ID NO: 53 |
| GGDYTCRMGPITWICTKAGG | SEQ ID NO: 54 |
| GGVYSCRMGPTTWECNRYVG | SEQ ID NO: 55 |
| GGAYLCHMGPITWVCRPQGG | SEQ ID NO: 56 |
| GGEYSCRMGPNTWVCKPVGG | SEQ ID NO: 57 |
| GGLYLCRMGPVTWECQPRGG | SEQ ID NO: 58 |
| GGLYTCRMGPITWVCLLPGG | SEQ ID NO: 59 |
| GGLYTCRMGPVTWVCTGAGG | SEQ ID NO: 60 |

FIG. 9 (B)

| | |
|---|---|
| GGVYKCRMGPLTWECRPTGG | SEQ ID NO: 61 |
| GGDYNCRFGPLTWVCKPSGG | SEQ ID NO: 62 |
| GGSYLCRFGPTTWLCSSAGG | SEQ ID NO: 63 |
| GGSYLCRMGPTTWVCTRMGG | SEQ ID NO: 64 |
| GGSYLCRFGPTTWLCTQRGG | SEQ ID NO: 65 |
| GGWVTCRMGPITWVCGVHGG | SEQ ID NO: 66 |
| GGQLLCGIGPITWVCRWVGG | SEQ ID NO: 67 |
| GGKYSCFMGPTTWVCSPVGRGV | SEQ ID NO: 68 |
| GGWVYCRIGPITWVCDTNGG | SEQ ID NO: 69 |
| GGMYYCRMGPMTWVCKGAGG | SEQ ID NO: 70 |
| GGTTQCWIGPITWVCRARGG | SEQ ID NO: 71 |
| GGPYHCRMGPITWVCGPVGG | SEQ ID NO: 72 |
| GGEYRCRMGPISWVCSPQGG | SEQ ID NO: 73 |
| GGNYTCRFGPLTWECTPQGGGA | SEQ ID NO: 74 |
| GGSWDCRIGPITWVCKWSGG | SEQ ID NO: 75 |
| VGNYMCHFGPITWVCRPGGG | SEQ ID NO: 76 |
| GGLYLCRMGPQTWMCQPGGG | SEQ ID NO: 77 |
| GGDYVCRMGPMTWVCAPYGR | SEQ ID NO: 78 |
| GGWYSCLMGPMTWVCKAHRG | SEQ ID NO: 79 |
| GGKYYCWMGPMTWVCSPAGG | SEQ ID NO: 80 |
| GGYVMCRIGPITWVCDIPGG | SEQ ID NO: 81 |
| GSCLQCCIGPITWVCRHAGG | SEQ ID NO: 82 |
| GGNYFCRMGPITWVCCPSVG | SEQ ID NO: 83 |
| GGEYICRMGPLTWECKRTGG | SEQ ID NO: 84 |
| GGLYACRMGPITWVCKYMAG | SEQ ID NO: 85 |
| GGQYLCTFGPITWLCRGAGG | SEQ ID NO: 86 |
| GGVYACRMGPITWVCSPLGG | SEQ ID NO: 87 |
| GGYTTCRMGPITWVCSAHGG | SEQ ID NO: 88 |
| GGTYKCWMGPMTWVCRPVGG | SEQ ID NO: 89 |
| GGNYYCRFGPITFECHPTGG | SEQ ID NO: 90 |
| GGEYLCRMGPMTWVCTPVGG | SEQ ID NO: 91 |
| GGLYTCRMGPITWVCLPAGG | SEQ ID NO: 92 |
| GGLYTCRMGPITWVCLPAGG | SEQ ID NO: 93 |

SEQUENCE LISTING ( 1 ) GENERAL INFORMATION:

( i i i ) NUMBER OF SEQUENCES: 93

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..10
        ( D ) OTHER INFORMATION: /note= "Xaa(Pos1) can be C,A,'-amino-y-
            bromobutyric acid or Hoc; Xaa(Pos2) can be R,H,L or W;
            Xaa(Pos3) can be M,F or I; Xaa(Pos6) can be any one of
            the 20 L- amino acids or the stereoisomeric D-amino acids;
            Xaa(Pos9) can be D,E,I,L or V; and Xaa(Pos10) can be
            C,A,'-amino- y-bromobutyric acid or Hoc, provided that
            either Xaa(Pos1) or Xaa(Pos10) is C or Hoc"

( x i ) SEQUENCE DESCRIPTION: SEQ ID NO:1:

```
Xaa  Xaa  Xaa  Gly  Pro  Xaa  Thr  Trp  Xaa  Xaa
1                  5                       10
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..12
        ( D ) OTHER INFORMATION: /note= "Xaa(Pos2) and Xaa(Pos8) can be
            any one of the 20 L-amino acids; Xaa(Pos3) can be
            C,A,'-amino- y- bromobutyric acid or Hoc; Xaa(Pos4) can be
            R,H,L or W; Xaa(Pos5) can be M,F or I; Xaa(Pos11) can be
            D,E,I,L or V; and Xaa(Pos12) can be C,A,'-amino-y-
            bromobutyric acid or Hoc, provided that either Xaa(Pos3)
            or Xaa(Pos12) is C or Hoc"

( x i ) SEQUENCE DESCRIPTION: SEQ ID NO:2:

```
Tyr  Xaa  Xaa  Xaa  Xaa  Gly  Pro  Xaa  Thr  Trp  Xaa  Xaa
1                  5                        10
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide (B) LOCATION: 1..16
(D) OTHER INFORMATION: /note= "Xaa(Pos1), Xaa(Pos 3),
Xaa(Pos9), Xaa(Pos14), Xaa(Pos15) and Xaa(Pos16) can be
any one of 20 L-amino acids; Xaa(Pos4) can be
C,A,'-amino- γ-bromobutyric acid or Hoc; Xaa(Pos5) can be
R,H,L or W; Xaa(Pos6) can be M,F or I; Xaa(Pos12) can be
D,E,I,L or V; and Xaa(Pos13) can be C,A,'-amino-γ-
bromobutyric acid or Hoc, provided that either Xaa(Pos4)
or Xaa(Pos13) is C or Hoc"

(xi) SEQUENCE DESCRIPTION: SEQ ID NO:3:

```
Xaa Tyr Xaa Xaa Xaa Xaa Gly Pro Xaa Thr Trp Xaa Xaa Xaa Xaa Xaa
1               5                   10                  15
```

(2) INFORMATION FOR SEQ ID NO:4:

(i) SEQUENCE CHARACTERISTICS:
  (A) LENGTH: 16 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:4:

```
Xaa Tyr Xaa Cys Xaa Xaa Gly Pro Xaa Thr Trp Xaa Cys Xaa Xaa Xaa
1               5                   10                  15
```

(2) INFORMATION FOR SEQ ID NO:5:

(i) SEQUENCE CHARACTERISTICS:
  (A) LENGTH: 16 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Peptide
  (B) LOCATION: 1..16
  (D) OTHER INFORMATION: /note= "Xaa(Pos1), Xaa(Pos3) and
    Xaa(Pos16) can be any one of the 20 L-amino acids;
    Xaa(Pos5) can be R or H; Xaa(Pos6) can be F or M;
    Xaa(Pos9) can be I,L,T,M or V; Xaa(Pos12) can be D or V;
    Xaa(Pos14) can be G,K,L,Q,R,S or T; Xaa(Pos15) can be
    A,G,P,R or Y"

(xi) SEQUENCE DESCRIPTION: SEQ ID NO:5:

```
Xaa Tyr Xaa Cys Xaa Xaa Gly Pro Xaa Thr Trp Xaa Cys Xaa Xaa Xaa
1               5                   10                  15
```

(2) INFORMATION FOR SEQ ID NO:6:

(i) SEQUENCE CHARACTERISTICS:
  (A) LENGTH: 16 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Peptide
  (B) LOCATION: 1..16
  (D) OTHER INFORMATION: /note= "Xaa(Pos1) can be D,E,L,N,S,T or
    V; Xaa(Pos3) can be A,H,K,L,M,S or T; Xaa(Pos5) can be R
    or H; Xaa(Pos6) can be F or M; Xaa(Pos9) can be I,L,T,M
    or V; Xaa(Pos12) can be D or V; Xaa(Pos14) can be K,R,S
    or T; Xaa(Pos15) is P and Xaa(Pos16) can be any one of
    the 20 L- amino acids"

(xi) SEQUENCE DESCRIPTION: SEQ ID NO:6:

```
Xaa  Tyr  Xaa  Cys  Xaa  Xaa  Gly  Pro  Xaa  Thr  Trp  Xaa  Cys  Xaa  Xaa  Xaa
 1                   5                        10                      15
```

( 2 ) INFORMATION FOR SEQ ID NO:7:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Gly  Gly  Leu  Tyr  Leu  Cys  Arg  Phe  Gly  Pro  Val  Thr  Trp  Asp  Cys  Gly
 1              5                        10                      15

Tyr  Lys  Gly  Gly
               20
```

( 2 ) INFORMATION FOR SEQ ID NO:8:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Gly  Gly  Thr  Tyr  Ser  Cys  His  Phe  Gly  Pro  Leu  Thr  Trp  Val  Cys  Lys
 1              5                        10                      15

Pro  Gln  Gly  Gly
               20
```

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Gly  Gly  Asp  Tyr  His  Cys  Arg  Met  Gly  Pro  Leu  Thr  Trp  Val  Cys  Lys
 1              5                        10                      15

Pro  Leu  Gly  Gly
               20
```

( 2 ) INFORMATION FOR SEQ ID NO:10:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Val  Gly  Asn  Tyr  Met  Cys  His  Phe  Gly  Pro  Ile  Thr  Trp  Val  Cys  Arg
 1              5                        10                      15

Pro  Gly  Gly  Gly
               20
```

( 2 ) INFORMATION FOR SEQ ID NO:11:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Gly Gly Val Tyr Ala Cys Arg Met Gly Pro Ile Thr Trp Val Cys Ser
1               5                   10                  15
Pro Leu Gly Gly
            20
```

( 2 ) INFORMATION FOR SEQ ID NO:12:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Val Gly Asn Tyr Met Ala His Met Gly Pro Ile Thr Trp Val Cys Arg
1               5                   10                  15
Pro Gly Gly
```

( 2 ) INFORMATION FOR SEQ ID NO:13:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Gly Gly Thr Tyr Ser Cys His Phe Gly Pro Leu Thr Trp Val Cys Lys
1               5                   10                  15
Pro Gln
```

( 2 ) INFORMATION FOR SEQ ID NO:14:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Gly Gly Leu Tyr Ala Cys His Met Gly Pro Met Thr Trp Val Cys Gln
1               5                   10                  15
Pro Leu Arg Gly
            20
```

( 2 ) INFORMATION FOR SEQ ID NO:15:

( i ) SEQUENCE CHARACTERISTICS:
        ( A ) LENGTH: 22 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:15:

Thr Ile Ala Gln Tyr Ile Cys Tyr Met Gly Pro Glu Thr Trp Glu Cys
1               5                   10                  15

Arg Pro Ser Pro Lys Ala
            20

(2) INFORMATION FOR SEQ ID NO:16:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Thr Ser Cys His Phe Gly Pro Leu Thr Trp Val Cys Lys
1               5                   10

(2) INFORMATION FOR SEQ ID NO:17:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Tyr Cys His Phe Gly Pro Leu Thr Trp Val Cys
1               5                   10

(2) INFORMATION FOR SEQ ID NO:18:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Ser Cys His Phe Gly Pro Leu Thr Trp Val Cys Lys
1               5                   10

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..12
        (D) OTHER INFORMATION: /note= "Xaa(Pos1) can be any one of the
            20 L-amino acids; except that Xaa(Pos1) may or may not be
            Y and Xaa(Pos1) may be any non-naturally occurring
            aromatic acid analog when Xaa(Pos1) is Y. Xaa(Pos2) and
            Xaa(Pos8) can be any one of the 20 L-amino acids;
            Xaa(Pos3) can be C,A,'-amino-y-bromobutyric acid or Hoc;

Xaa(Pos4) can be R,H,L or W; Xaa(Pos5) can be M,F or I;
Xaa(Pos11) can be D,E,I,L or V and Xaa(Pos12) can be
C,A,'-amino- y-bromobutyric acid or Hoc provided that
either Xaa(Pos3) or Xaa(Pos12) is C or Hoc"

( x i ) SEQUENCE DESCRIPTION: SEQ ID NO:19:

```
Xaa Xaa Xaa Xaa Xaa Gly Pro Xaa Thr Trp Xaa Xaa
 1               5                   10
```

( 2 ) INFORMATION FOR SEQ ID NO:20:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
Gly Gly Thr Tyr Ser Cys His Phe Gly Pro Leu Thr Trp Val Cys Lys
 1               5                   10                  15
Pro Gln Gly Gly
            20
```

( 2 ) INFORMATION FOR SEQ ID NO:21:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

```
Gly Gly Thr Tyr Arg Cys Ser Met Gly Pro Met Thr Trp Val Cys Leu
 1               5                   10                  15
Pro Met Gly Gly
            20
```

( 2 ) INFORMATION FOR SEQ ID NO:22:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Gly Gly Met Tyr Ser Cys Arg Met Gly Pro Met Thr Trp Val Cys Gly
 1               5                   10                  15
Pro Ser Gly Gly
            20
```

( 2 ) INFORMATION FOR SEQ ID NO:23:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

```
Gly Gly Trp Ala Trp Cys Arg Met Gly Pro Ile Thr Trp Val Cys Ser
 1               5                   10                  15

Ala His Gly Gly
            20
```

(2) INFORMATION FOR SEQ ID NO:24:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Gly Gly Met Tyr Ser Cys Arg Met Gly Pro Met Thr Trp Val Cys Ile
 1               5                   10                  15

Pro Tyr Gly Gly
            20
```

(2) INFORMATION FOR SEQ ID NO:25:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Gly Gly Glu Tyr Lys Cys Tyr Met Gly Pro Ile Thr Trp Val Cys Lys
 1               5                   10                  15

Pro Glu Gly Gly
            20
```

(2) INFORMATION FOR SEQ ID NO:26:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Gly Gly Asp Tyr Thr Cys Arg Met Gly Pro Met Thr Trp Ile Cys Thr
 1               5                   10                  15

Ala Thr Gly Gly
            20
```

(2) INFORMATION FOR SEQ ID NO:27:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Gly Gly Asn Tyr Leu Cys Arg Phe Gly Pro Gly Thr Trp Asp Cys Thr
 1               5                   10                  15

Gly Phe Arg Gly
```

20

(2) INFORMATION FOR SEQ ID NO:28:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Gly Gly Asn Tyr Val Cys Arg Met Gly Pro Ile Thr Trp Ile Cys Thr
 1               5                  10                  15
Pro Ala Gly Gly
            20
```

(2) INFORMATION FOR SEQ ID NO:29:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

```
Gly Gly Lys Asp Val Cys Arg Met Gly Pro Ile Thr Trp Asp Cys Arg
 1               5                  10                  15
Ser Thr Gly Gly
            20
```

(2) INFORMATION FOR SEQ ID NO:30:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Gly Gly Ser Tyr Leu Cys Arg Met Gly Pro Thr Thr Trp Leu Cys Thr
 1               5                  10                  15
Ala Gln Arg Gly Gly Gly Asn
            20
```

(2) INFORMATION FOR SEQ ID NO:31:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

```
Gly Gly Asn Tyr Leu Cys Arg Met Gly Pro Ala Thr Trp Val Cys Gly
 1               5                  10                  15
Arg Met Gly Gly
            20
```

(2) INFORMATION FOR SEQ ID NO:32:

( i ) SEQUENCE CHARACTERISTICS:
   ( A ) LENGTH: 20 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:32:

```
Gly Gly Glu Tyr Lys Cys Arg Met Gly Pro Leu Thr Trp Val Cys Gln
1               5                   10                  15
Tyr Ala Gly Gly
            20
```

( 2 ) INFORMATION FOR SEQ ID NO:33:

( i ) SEQUENCE CHARACTERISTICS:
   ( A ) LENGTH: 20 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:33:

```
Gly Gly Asp Tyr Thr Cys Arg Met Gly Pro Met Thr Trp Ile Cys Thr
1               5                   10                  15
Ala Thr Arg Gly
            20
```

( 2 ) INFORMATION FOR SEQ ID NO:34:

( i ) SEQUENCE CHARACTERISTICS:
   ( A ) LENGTH: 20 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:34:

```
Gly Gly Val Tyr Val Cys Arg Met Gly Pro Leu Thr Trp Glu Cys Thr
1               5                   10                  15
Ala Ser Gly Gly
            20
```

( 2 ) INFORMATION FOR SEQ ID NO:35:

( i ) SEQUENCE CHARACTERISTICS:
   ( A ) LENGTH: 20 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:35:

```
Gly Gly Glu Tyr Ser Cys Arg Met Gly Pro Met Thr Trp Val Cys Ser
1               5                   10                  15
Pro Thr Gly Gly
            20
```

( 2 ) INFORMATION FOR SEQ ID NO:36:

( i ) SEQUENCE CHARACTERISTICS:
   ( A ) LENGTH: 20 amino acids
   ( B ) TYPE: amino acid -continued (C) STRANDEDNESS: single
        (D) TOPOLOGY: linear (ii) MOLECULE TYPE: peptide (xi) SEQUENCE DESCRIPTION: SEQ ID NO:36:

Gly Gly Glu Tyr Leu Cys Arg Met Gly Pro Ile Thr Trp Val Cys Glu
1               5                   10                  15

Arg Tyr Gly Gly
            20

(2) INFORMATION FOR SEQ ID NO:37:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Gly Gly Asn Tyr Ile Cys Arg Met Gly Pro Met Thr Trp Val Cys Thr
1               5                   10                  15

Ala His Gly Gly
            20

(2) INFORMATION FOR SEQ ID NO:38:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Gly Gly Asp Tyr Leu Cys Arg Met Gly Pro Ala Thr Trp Val Cys Gly
1               5                   10                  15

Arg Met Gly Gly
            20

(2) INFORMATION FOR SEQ ID NO:39:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

Gly Gly Leu Tyr Leu Cys Arg Phe Gly Pro Val Thr Trp Asp Cys Gly
1               5                   10                  15

Tyr Lys Gly Gly
            20

(2) INFORMATION FOR SEQ ID NO:40:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:40:

Gly Gly Leu Tyr Ser Cys Arg Met Gly Pro Ile Thr Trp Val Cys Thr
1               5                   10                  15

Lys Ala Gly Gly
            20

( 2 ) INFORMATION FOR SEQ ID NO:41:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:41:

Gly Gly Gly Tyr His Cys Arg Met Gly Pro Met Thr Trp Val Cys Arg
1               5                   10                  15

Pro Val Gly Gly
            20

( 2 ) INFORMATION FOR SEQ ID NO:42:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:42:

Gly Gly Thr Tyr Ser Cys His Phe Gly Pro Leu Thr Trp Val Cys Lys
1               5                   10                  15

Pro Gln Gly Gly
            20

( 2 ) INFORMATION FOR SEQ ID NO:43:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:43:

Gly Gly Ile Tyr Lys Cys Leu Met Gly Pro Leu Thr Trp Val Cys Thr
1               5                   10                  15

Pro Asp Gly Gly
            20

( 2 ) INFORMATION FOR SEQ ID NO:44:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:44:

Gly Gly Leu Tyr Ser Cys Leu Met Gly Pro Ile Thr Trp Leu Cys Lys

```
               1               5                    10                   15
            Pro Lys Gly Gly
                        20
```

( 2 ) INFORMATION FOR SEQ ID NO:45:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:45:

```
Gly Gly Asp Tyr His Cys Arg Met Gly Pro Leu Thr Trp Val Cys Lys
 1               5                    10                   15
Pro Leu Gly Gly
            20
```

( 2 ) INFORMATION FOR SEQ ID NO:46:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:46:

```
Gly Gly Asp Tyr Ser Cys Arg Met Gly Pro Thr Thr Trp Val Cys Thr
 1               5                    10                   15
Pro Pro Gly Gly
            20
```

( 2 ) INFORMATION FOR SEQ ID NO:47:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:47:

```
Gly Gly Asp Tyr Trp Cys Arg Met Gly Pro Ser Thr Trp Glu Cys Asn
 1               5                    10                   15
Ala His Gly Gly
            20
```

( 2 ) INFORMATION FOR SEQ ID NO:48:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

```
Gly Gly Lys Tyr Leu Cys Ser Phe Gly Pro Ile Thr Trp Val Cys Ala
 1               5                    10                   15
Arg Tyr Gly Gly
            20
```

( 2 ) INFORMATION FOR SEQ ID NO:49:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

```
Gly  Gly  Leu  Tyr  Lys  Cys  Arg  Leu  Gly  Pro  Ile  Thr  Trp  Val  Cys  Ser
1                   5                        10                       15
Pro  Leu  Gly  Gly
               20
```

( 2 ) INFORMATION FOR SEQ ID NO:50:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:50:

```
Gly  Gly  Ser  Tyr  Thr  Cys  Arg  Phe  Gly  Pro  Glu  Thr  Trp  Val  Cys  Arg
1                   5                        10                       15
Pro  Asn  Gly  Gly
               20
```

( 2 ) INFORMATION FOR SEQ ID NO:51:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:51:

```
Gly  Gly  Ser  Tyr  Ser  Cys  Arg  Met  Gly  Pro  Ile  Thr  Trp  Val  Cys  Lys
1                   5                        10                       15
Pro  Gly  Gly  Gly
               20
```

( 2 ) INFORMATION FOR SEQ ID NO:52:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:52:

```
Gly  Gly  Ser  Tyr  Thr  Cys  Arg  Met  Gly  Pro  Ile  Thr  Trp  Val  Cys  Leu
1                   5                        10                       15
Pro  Ala  Gly  Gly
               20
```

( 2 ) INFORMATION FOR SEQ ID NO:53:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:53:

Gly Gly Leu Tyr Glu Cys Arg Met Gly Pro Met Thr Trp Val Cys Arg
1               5                   10                  15
Pro Gly Gly Gly
            20

( 2 ) INFORMATION FOR SEQ ID NO:54:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:54:

Gly Gly Asp Tyr Thr Cys Arg Met Gly Pro Ile Thr Trp Ile Cys Thr
1               5                   10                  15
Lys Ala Gly Gly
            20

( 2 ) INFORMATION FOR SEQ ID NO:55:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:55:

Gly Gly Val Tyr Ser Cys Arg Met Gly Pro Thr Thr Trp Glu Cys Asn
1               5                   10                  15
Arg Tyr Val Gly
            20

( 2 ) INFORMATION FOR SEQ ID NO:56:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:56:

Gly Gly Ala Tyr Leu Cys His Met Gly Pro Ile Thr Trp Val Cys Arg
1               5                   10                  15
Pro Gln Gly Gly
            20

( 2 ) INFORMATION FOR SEQ ID NO:57:

( i ) SEQUENCE CHARACTERISTICS:
  ( A ) LENGTH: 20 amino acids
  ( B ) TYPE: amino acid
  ( C ) STRANDEDNESS: single ( D ) TOPOLOGY: linear ( i i ) MOLECULE TYPE: peptide ( x i ) SEQUENCE DESCRIPTION: SEQ ID NO:57:

```
Gly Gly Glu Tyr Ser Cys Arg Met Gly Pro Asn Thr Trp Val Cys Lys
1               5                   10                  15
Pro Val Gly Gly
            20
```

( 2 ) INFORMATION FOR SEQ ID NO:58:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:58:

```
Gly Gly Leu Tyr Leu Cys Arg Met Gly Pro Val Thr Trp Glu Cys Gln
1               5                   10                  15
Pro Arg Gly Gly
            20
```

( 2 ) INFORMATION FOR SEQ ID NO:59:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:59:

```
Gly Gly Leu Tyr Thr Cys Pro Met Gly Pro Ile Thr Trp Val Cys Leu
1               5                   10                  15
Leu Pro Gly Gly
            20
```

( 2 ) INFORMATION FOR SEQ ID NO:60:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:60:

```
Gly Gly Leu Tyr Thr Cys Arg Met Gly Pro Val Thr Trp Val Cys Thr
1               5                   10                  15
Gly Ala Gly Gly
            20
```

( 2 ) INFORMATION FOR SEQ ID NO:61:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide 5,767,078

51

52

-continued ( x i ) SEQUENCE DESCRIPTION: SEQ ID NO:61:

Gly Gly Val Tyr Lys Cys Arg Met Gly Pro Leu Thr Trp Glu Cys Arg
1               5                   10                  15

Pro Thr Gly Gly
            20

( 2 ) INFORMATION FOR SEQ ID NO:62:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:62:

Gly Gly Asp Tyr Asn Cys Arg Phe Gly Pro Leu Thr Trp Val Cys Lys
1               5                   10                  15

Pro Ser Gly Gly
            20

( 2 ) INFORMATION FOR SEQ ID NO:63:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:63:

Gly Gly Ser Tyr Leu Cys Arg Phe Gly Pro Thr Thr Trp Leu Cys Ser
1               5                   10                  15

Ser Ala Gly Gly
            20

( 2 ) INFORMATION FOR SEQ ID NO:64:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:64:

Gly Gly Ser Tyr Leu Cys Arg Met Gly Pro Thr Thr Trp Val Cys Thr
1               5                   10                  15

Arg Met Gly Gly
            20

( 2 ) INFORMATION FOR SEQ ID NO:65:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:65:

Gly Gly Ser Tyr Leu Cys Arg Phe Gly Pro Thr Thr Trp Leu Cys Thr
1               5                   10                  15

```
        Gln  Arg  Gly  Gly
                    20
```

( 2 ) INFORMATION FOR SEQ ID NO:66:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:66:

```
Gly  Gly  Trp  Val  Thr  Cys  Arg  Met  Gly  Pro  Ile  Thr  Trp  Val  Cys  Gly
 1                    5                         10                         15

Val  His  Gly  Gly
               20
```

( 2 ) INFORMATION FOR SEQ ID NO:67:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:67:

```
Gly  Gly  Gln  Leu  Leu  Cys  Gly  Ile  Gly  Pro  Ile  Thr  Trp  Val  Cys  Arg
 1                    5                         10                         15

Trp  Val  Gly  Gly
               20
```

( 2 ) INFORMATION FOR SEQ ID NO:68:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:68:

```
Gly  Gly  Lys  Tyr  Ser  Cys  Phe  Met  Gly  Pro  Thr  Thr  Trp  Val  Cys  Ser
 1                    5                         10                         15

Pro  Val  Gly  Arg  Gly  Val
               20
```

( 2 ) INFORMATION FOR SEQ ID NO:69:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:69:

```
Gly  Gly  Trp  Val  Tyr  Cys  Arg  Ile  Gly  Pro  Ile  Thr  Trp  Val  Cys  Asp
 1                    5                         10                         15

Thr  Asn  Gly  Gly
               20
```

( 2 ) INFORMATION FOR SEQ ID NO:70:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:70:

```
Gly Gly Met Tyr Tyr Cys Arg Met Gly Pro Met Thr Trp Val Cys Lys
 1               5                  10                  15
Gly Ala Gly Gly
            20
```

( 2 ) INFORMATION FOR SEQ ID NO:71:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:71:

```
Gly Gly Thr Thr Gln Cys Trp Ile Gly Pro Ile Thr Trp Val Cys Arg
 1               5                  10                  15
Ala Arg Gly Gly
            20
```

( 2 ) INFORMATION FOR SEQ ID NO:72:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:72:

```
Gly Gly Pro Tyr His Cys Arg Met Gly Pro Ile Thr Trp Val Cys Gly
 1               5                  10                  15
Pro Val Gly Gly
            20
```

( 2 ) INFORMATION FOR SEQ ID NO:73:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:73:

```
Gly Gly Glu Tyr Arg Cys Arg Met Gly Pro Ile Ser Trp Val Cys Ser
 1               5                  10                  15
Pro Gln Gly Gly
            20
```

( 2 ) INFORMATION FOR SEQ ID NO:74:

( i ) SEQUENCE CHARACTERISTICS:

(A) LENGTH: 22 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:74:

Gly Gly Asn Tyr Thr Cys Arg Phe Gly Pro Leu Thr Trp Glu Cys Thr
1               5                   10                  15
Pro Gln Gly Gly Gly Ala
            20

(2) INFORMATION FOR SEQ ID NO:75:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:75:

Gly Gly Ser Trp Asp Cys Arg Ile Gly Pro Ile Thr Trp Val Cys Lys
1               5                   10                  15
Trp Ser Gly Gly
            20

(2) INFORMATION FOR SEQ ID NO:76:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:76:

Val Gly Asn Tyr Met Cys His Phe Gly Pro Ile Thr Trp Val Cys Arg
1               5                   10                  15
Pro Gly Gly Gly
            20

(2) INFORMATION FOR SEQ ID NO:77:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:77:

Gly Gly Leu Tyr Leu Cys Arg Met Gly Pro Gln Thr Trp Met Cys Gln
1               5                   10                  15
Pro Gly Gly Gly
            20

(2) INFORMATION FOR SEQ ID NO:78:

(i) SEQUENCE CHARACTERISTICS:
(A) LENGTH: 20 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:78:

Gly Gly Asp Tyr Val Cys Arg Met Gly Pro Met Thr Trp Val Cys Ala
    1               5                   10                  15

Pro Tyr Gly Arg
                20

( 2 ) INFORMATION FOR SEQ ID NO:79:

( i ) SEQUENCE CHARACTERISTICS:
            ( A ) LENGTH: 20 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:79:

Gly Gly Trp Tyr Ser Cys Leu Met Gly Pro Met Thr Trp Val Cys Lys
    1               5                   10                  15

Ala His Arg Gly
                20

( 2 ) INFORMATION FOR SEQ ID NO:80:

( i ) SEQUENCE CHARACTERISTICS:
            ( A ) LENGTH: 20 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:80:

Gly Gly Lys Tyr Tyr Cys Trp Met Gly Pro Met Thr Trp Val Cys Ser
    1               5                   10                  15

Pro Ala Gly Gly
                20

( 2 ) INFORMATION FOR SEQ ID NO:81:

( i ) SEQUENCE CHARACTERISTICS:
            ( A ) LENGTH: 20 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:81:

Gly Gly Tyr Val Met Cys Arg Ile Gly Pro Ile Thr Trp Val Cys Asp
    1               5                   10                  15

Ile Pro Gly Gly
                20

( 2 ) INFORMATION FOR SEQ ID NO:82:

( i ) SEQUENCE CHARACTERISTICS:
            ( A ) LENGTH: 20 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:82:

```
         Gly  Ser  Cys  Leu  Gln  Cys  Cys  Ile  Gly  Pro  Ile  Thr  Trp  Val  Cys  Arg
         1                  5                             10                            15

His  Ala  Gly  Gly
                       20
```

( 2 ) INFORMATION FOR SEQ ID NO:83:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:83:

```
         Gly  Gly  Asn  Tyr  Phe  Cys  Arg  Met  Gly  Pro  Ile  Thr  Trp  Val  Cys  Gln
         1                  5                             10                            15

Arg  Ser  Val  Gly
                       20
```

( 2 ) INFORMATION FOR SEQ ID NO:84:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:84:

```
         Gly  Gly  Glu  Tyr  Ile  Cys  Arg  Met  Gly  Pro  Leu  Thr  Trp  Glu  Cys  Lys
         1                  5                             10                            15

Arg  Thr  Gly  Gly
                       20
```

( 2 ) INFORMATION FOR SEQ ID NO:85:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:85:

```
         Gly  Gly  Leu  Tyr  Ala  Cys  Arg  Met  Gly  Pro  Ile  Thr  Trp  Val  Cys  Lys
         1                  5                             10                            15

Tyr  Met  Ala  Gly
                       20
```

( 2 ) INFORMATION FOR SEQ ID NO:86:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:86:

```
         Gly  Gly  Gln  Tyr  Leu  Cys  Thr  Phe  Gly  Pro  Ile  Thr  Trp  Leu  Cys  Arg
         1                  5                             10                            15
```

Gly Ala Gly Gly
          20

( 2 ) INFORMATION FOR SEQ ID NO:87:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:87:

Gly Gly Val Tyr Ala Cys Arg Met Gly Pro Ile Thr Trp Val Cys Ser
1               5                   10                  15
Pro Leu Gly Gly
          20

( 2 ) INFORMATION FOR SEQ ID NO:88:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:88:

Gly Gly Tyr Thr Thr Cys Arg Met Gly Pro Ile Thr Trp Val Cys Ser
1               5                   10                  15
Ala His Gly Gly
          20

( 2 ) INFORMATION FOR SEQ ID NO:89:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:89:

Gly Gly Thr Tyr Lys Cys Trp Met Gly Pro Met Thr Trp Val Cys Arg
1               5                   10                  15
Pro Val Gly Gly
          20

( 2 ) INFORMATION FOR SEQ ID NO:90:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:90:

Gly Gly Asn Tyr Tyr Cys Arg Phe Gly Pro Ile Thr Phe Glu Cys His
1               5                   10                  15
Pro Thr Gly Gly
          20

(2) INFORMATION FOR SEQ ID NO:91:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:91:

Gly Gly Glu Tyr Leu Cys Arg Met Gly Pro Asn Thr Trp Val Cys Thr
1               5                   10                  15

Pro Val Gly Gly
            20

(2) INFORMATION FOR SEQ ID NO:92:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:92:

Gly Gly Leu Tyr Thr Cys Arg Met Gly Pro Ile Thr Trp Val Cys Leu
1               5                   10                  15

Pro Ala Gly Gly
            20

(2) INFORMATION FOR SEQ ID NO:93:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:93:

Gly Gly Leu Tyr Thr Cys Arg Met Gly Pro Ile Thr Trp Val Cys Leu
1               5                   10                  15

Pro Ala Gly Gly
            20

AGONIST PEPTIDE DIMERS

FIELD OF THE INVENTION

The present invention is directed to the dimerization of agonists and antagonists of cell surface receptors and particularly to peptide dimers which behave as cell surface receptor agonists in their dimeric form. Such receptors belong to the dimerization-mediated activation class often observed among receptors for growth and differentiation factors. The agonists of this class of receptors is understood to effect dimerization of the receptor and thus signal initiation. The present invention exemplifies dimers of erythropoietin (EPO) agonists and antagonists comprising a core amino acid sequence of $X_3X_4X_5GPX_6TWX_7X_8$ (SEQ ID NO: 1) wherein each amino acid is indicated by standard one letter abbreviation; $X_3$ can be C, A, α-amino-γ-bromobutyric acid or Hoc; $X_4$ can be R, H, L or W; $X_5$ can be M, F, or I; $X_6$ is independently selected from any one of the 20 genetically coded L-amino acids or the stereoisomeric D-amino acids; $X_7$ can be D, E, I, L or V; and $X_8$ can be C, A, α-amino-γ-bromobutyric acid or Hoc, provided that either $X_3$ or $X_8$ is C or Hoc.

BACKGROUND OF THE INVENTION

Erythropoietin (EPO) is a glycoprotein hormone with an approximate molecular weight of 34,000 daltons. The primary role of EPO, which is synthesized in the kidneys of mammals, is to stimulate mitotic cell division and differentiation of erythrocyte precursor cells. As a result, EPO acts to stimulate and to regulate the production of erythrocytes. Erythrocytes, and the hemoglobin contained therein, play a central role in supplying oxygen to the body. Thus, the stimulation of erythrocyte production is able to increase the oxygen-carrying capacity of the blood.

During normal conditions, EPO is present in very low concentrations in plasma. Under hypoxic conditions, the amount of EPO in the circulation is increased in response to reduced $O_2$ blood levels. Hypoxia may be caused from various conditions including the loss of large amounts of blood, destruction of red blood cells by over-exposure to radiation or chemotherapeutic agents, reduction in oxygen intake due to high altitudes or prolonged unconsciousness, or by various forms of anemia. As the hypoxic condition diminishes, the amount of EPO produced subsequently diminishes.

Because of the essential role of EPO in red blood cell formation, the hormone is useful in both the diagnosis and the treatment of blood disorders characterized by low or defective red blood cell production. Recent studies provide a basis for the efficacy of EPO therapy in a variety of disease states, disorders, and states of hematologic irregularity, including: beta-thalassemia (See, Vedovato et al. (1984) *Acta. Haematol.* 71:211–213); cystic fibrosis (See, Vichinsky et al. (1984) *J. Pediatric* 105:15–21); pregnancy and menstrual disorders (See, Cotes et al. (1983) *Brit. J. Ostet. Gyneacol.* 90:304–311); early anemia of prematurity (See, Haga et al. (1983) *Acta Pediatr. Scand.* 72:827–831); spinal cord injury (See, Claus-Walker et al. (1984) *Arch. Phys. Med. Rehabil.* 65:370–374); space flight (See, Dunn et al. (1984) *Eur. J. Appl. Physiol.* 52:178–182); acute blood loss (See, Miller et al. (1982) *Brit. J. Haematol.* 52:545–590); aging (See, Udupa et al. (1984) *J. Lab. Clin. Med.* 103:574–588); various neoplastic disease states accompanied by abnormal erythropoiesis (See, Dainiak et al. (1983) *Cancer* 5:1101–1106); and renal insufficiency (See, Eschbach et al. (1987) *N. Eng. J. Med.* 316:73–78).

Although purified, homogenous EPO has been characterized, little is known about the mechanism of EPO-induced erythroblast proliferation and differentiation. The specific interaction of EPO with progenitor cells of immature red blood cells, platelets, and megakaryocytes has not been described. This is due in part, to the small number of surface EPO receptor molecules on normal erythroblasts and on the erythroleukemia cell lines. See Krantz and Goldwasser (1984) *Proc. Natl. Acad. Sci. USA*, 81:7574–7578; Branch et al. (1987) *Blood* 69:1782–1785; Mayeux et al. (1987) *FEBS Letters* 211:229–223; Mufson and Gesner (1987) *Blood* 69:1485–1490; Sakaguchi et al. (1987) *Biochem. Biophys. Res. Commun.* 146:7–12; Sawyer et al. (1987) *Proc. Natl. Acad. Sci. USA* 84:3690–3694; Sawyer et al. (1987) *J. Biol. Chem.* 262:5554–5562; and Todokoro et al. (1988) *Proc. Natl. Acad. Sci. USA* 84:4126–4130. The DNA sequences and encoded peptide sequences for murine and human EPO receptor proteins have been described. See, D'Andrea et al. PCT Patent Publication No. WO 90/08822 (published 1990).

The EPO-receptor (EPO-R) belongs to the class of growth-factor-type receptors which are activated by a ligand-induced protein dimerization. Other hormones and cytokines such as human growth hormone (hGH), granulocyte colony stimulating factor (G-CSF), epidermal growth factor (EGF) and insulin can cross-link two receptors resulting in juxtaposition of two cytoplasmic tails. Many of these dimerization-activated receptors have protein kinase domains within the cytoplasmic tails that phosphorylate the neighboring tail upon dimerization. While some cytoplasmic tails lack intrinsic kinase activity, these function by association with protein kinases. The EPO receptor is of the latter type. In each case, phosphorylation results in the activation of a signaling pathway.

In accordance with the present invention, it has been discovered that the dimerization of peptide agonists and antagonists of dimerization-mediated receptors, such as EPO-R, increase the biological efficacy relative to the biological activity of the 'monomeric' agonists and alters the properties of the antagonists such that, these dimers function as agonists, exhibiting biological activity.

SUMMARY OF THE INVENTION

In a first embodiment, the present invention is directed to peptide dimers which behave as cell-surface receptor agonists, dimers which exhibit binding and signal initiation of growth factor-type receptors. In one embodiment, the present invention provides peptide dimers which behave as EPO agonists. These dimers have two 'monomeric' peptide units of 10 to 40 or more amino acids, preferably 14 to about 20 residues in length, comprising a core amino acid sequence of $X_3X_4X_5GPX_6TWX_7X_8$ (SEQ ID NO: 1) where each amino acid is indicated by standard one letter abbreviation; $X_3$ can be C, A, α-amino-γ-bromobutyric acid, or Hoc, where Hoc is homocysteine; $X_4$ can be R, H, L, or W; $X_5$ can be M, F, or I; $X_6$ is independently selected from any one of the 20 genetically coded L-amino acids or the stereoisomeric D-amino acids; $X_7$ can be D, E, I, L, or V; and $X_8$ can be C, A, α-amino-γ-bromobutyric acid, or Hoc, where Hoc is homocysteine, provided that either $X_3$ or $X_8$ is C or Hoc. Preferably, the monomeric peptide unit of the dimer comprises a core sequence $YX_2X_3X_4X_5GPX_6TWX_7X_8$ (SEQ ID NO: 2) where each amino acid is indicated by standard one letter abbreviation; each $X_2$ and $X_6$ is independently selected from any one of the 20 genetically coded L-amino acids; $X_3$ can be C, A, α-amino-γ-bromobutyric acid, or Hoc, where Hoc is homocysteine; $X_4$ can be R, H, L, or W; $X_5$ can be M, F, or I; $X_7$ can be D, E, I, L, or V; and $X_8$ can be C, A, α-amino-γ-bromobutyric acid, or Hoc, where Hoc is homocysteine, provided that either $X_3$ or $X_8$ is C or Hoc.

More preferably, the monomeric peptide unit of the dimer comprises a core sequence of amino acids $X_1YX_2X_3$ $X_4X_5GPX_6TWX_7X_8X_9X_{10}X_{11}$ (SEQ ID NO: 3), where each amino acid is indicated by standard one letter abbreviation; each $X_1$, $X_2$, $X_6$, $X_9$, $X_{10}$, and $X_{11}$ is independently selected from any one of the 20 genetically coded L-amino acids; $X_3$ can be C, A, α-amino-γ-bromobutyric acid, or Hoc, where Hoc is homocysteine; $X_4$ can be R, H, L, or W; $X_5$ can be M, F, or I; $X_7$ can be D, E, I, L or V; and $X_8$ can be C, A, α-amino-γ-bromobutyric acid, or Hoc, where Hoc is homocysteine, provided that either $X_3$ or $X_8$ is C or Hoc.

In a more preferred embodiment, both $X_3$ and $X_8$ are C and thus, the monomeric peptide unit of the dimer comprises a core sequence of amino acids $X_1YX_2CX_4X_5GPX_6TWX_7$ $CX_9X_{10}X_{11}$ (SEQ ID NO: 4). More preferably, the monomeric peptide unit comprises a core sequence of amino acids $X_1YX_2CX_4X_5GPX_6TWX_7CX_9X_{10}X_{11}$ (SEQ ID NO: 5), where $X_4$ can be R or H; $X_5$ can be F or M; $X_6$ can be I, L, T, M, or V; $X_7$ is D or V; $X_9$ can be G, K, L, Q, R, S, or T; and $X_{10}$ can be A, G, P, R, or Y. In a most preferred embodiment, the monomeric peptide unit of the dimer will comprise a core sequence of amino acids $X_1YX_2CX_4X_5$ $GPX_6TWX_7CX_9X_{10}X_{11}$ (SEQ ID NO: 6), where $X_1$ can be D, E, L, N, S, T, or V; $X_2$ can be A, H, K, L, M, S, or T; $X_4$ is R or H; $X_9$ can be K, R, S, or T; and $X_{10}$ is P. Particularly preferred monomeric peptide units of the dimers include:

GGLYLCRFGPVTWDCGYKGG (SEQ ID NO: 7);
GGTYSCHFGPLTWVCKPQGG (SEQ ID NO: 8);
GGDYHCRMGPLTWVCKPLGG (SEQ ID NO: 9);
VGNYMCHFGPITWVCRPGGG (SEQ ID NO: 10);
GGVYACRMGPITWVCSPLGG (SEQ ID NO: 11);
VGNYMAHMGPITWVCRPGG (SEQ ID NO: 12);
GGTYSCHFGPLTWVCKPQ (SEQ ID NO: 13);
GGLYACHMGPMTWVCQPLRG (SEQ ID NO: 14);
TIAQYICYMGPETWECRPSPKA (SEQ ID NO: 15);
YSCHFGPLTWVCK (SEQ ID NO: 16);
YCHFGPLTWVC (SEQ ID NO: 17); and
SCHFGPLTWVCK (SEQ ID NO: 18).

Other particularly preferred monomeric peptide units of the present dimers include peptides comprising a core sequence of the formula $(X_0X_2)_nX_3X_4X_5GPX_6TWX_7X_8$ (SEQ ID NO: 19) wherein $X_2$ through $X_8$ are as previously defined herein (SEQ ID NO: 2), n is 1 or 0 and $X_0$ is any one of the naturally occurring L-amino acids except Y (tyrosine); n is defined herein as the number of occurrences of $(X_0X_2)$ which can be 1 or none in the core sequence. When $(X_0X_2)$ is present, i.e. when n=1, $X_0$ is not tyrosine and $X_0$ is not any non-naturally occurring aromatic amino acid analog. Such monomeric peptide units of the dimers of this invention can be prepared by truncating the peptides of FIG. 9, for example, from the N-terminus to delete the Y, tyrosine residue in SEQ ID NOS. 21–93. Such monomeric peptides can also be prepared by substitution of Y in position $X_0$ in the peptides of FIG. 9.

In accordance with the present invention the monomeric units of the dimers can be the same or different.

In a preferred embodiment polyethylene glycol (PEG) is employed as a linker to form the dimeric peptides of the present invention through a covalent bond.

In another embodiment, the present invention is directed to pharmaceutical compositions comprising at least one dimer peptide of the invention and a pharmaceutical carrier.

In a further embodiment, the present invention provides a method for therapeutically treating a mammal having a condition resulting from a hormone or growth factor deficiency by administration of at least one of the dimer peptides of the present invention.

In a still further embodiment, a method for therapeutically treating a mammal having a condition resulting from a deficiency of EPO or from reduced levels of blood oxygen caused by a decrease in erythrocyte number is provided.

In another embodiment of this invention, a method is provided for preparing agonists of cell-surface receptors wherein agonists of the class of cell-surface or dimerization-mediated receptors are dimerized to enhance the in vitro or in vivo biological activity of the cell-surface receptor relative to the monomeric agonists from which the dimer is derived. This method is also directed to the preparation of agonists of such growth-factor-type receptors by dimerizing antagonists of these receptors; the dimerized 'antagonists' thereby exhibit agonist biological activity in vitro and in vivo. In a preferred embodiment, the present method is directed to the preparation of EPO-R dimer agonists from monomeric EPO-R antagonists.

BRIEF DESCRIPTION OF THE DRAWINGS

FIG. 8 demonstrates the effect of PEG dimerization of peptide (SEQ ID NO: 18) activity in EPO responsive cell proliferation studies in FDC-P1 derived cell lines containing a human EPO receptor.

FIG. 9 provides the sequences of representative monomeric peptides of the present invention.

DETAILED DESCRIPTION OF THE INVENTION

Figure 1:
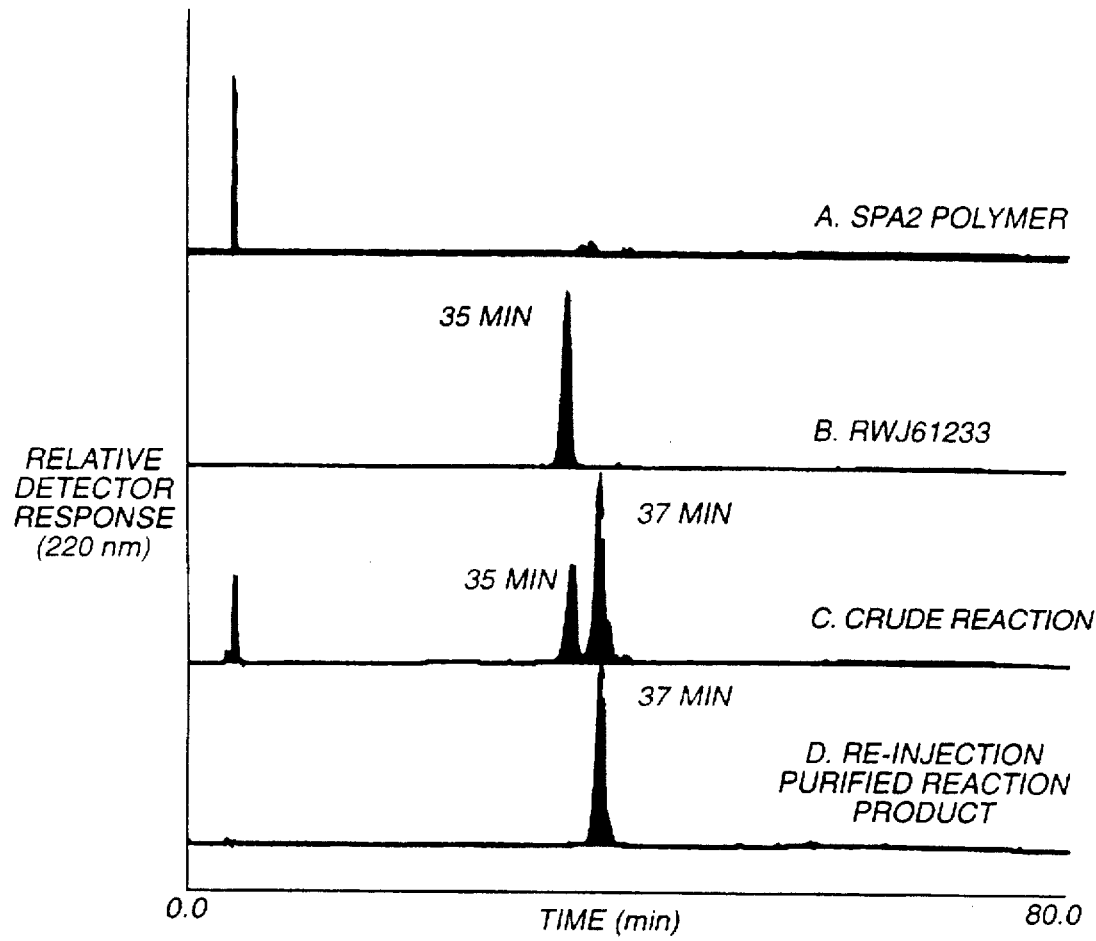
FIG. 1 shows a major peak, with a retention time of 37 minutes, of the dimerized EPO peptide, GGTYSCHFG-PLTWVCKPQGG (SEQ ID NO: 8)

The present invention is directed to peptide dimers which behave as cell surface receptor agonists, dimers which exhibit binding and signal initiation of growth-factor-type receptors. Sometimes called cell-surface receptors, growthfactor-type receptors or dimerization-mediated activator-receptors, these are a class of molecules which are understood to be activated by ligand-induced or ligand stabilized dimerization. Agonists of such receptors typically include large polypeptide hormones including the cytokines, insulin and various other growth or differentiation factors. The agonists are understood to induce dimerization of the receptor and thereby effect signal initiation. Such agonists are believed to effectively cross-link two receptors resulting in the repositioning of cytoplasmic tails which may directly or indirectly effect phosphorylation of the cytoplasmic tails and activation of a signaling pathway.

The present invention specifically includes those molecules which behave as agonists of cell-surface receptors when dimerized in accordance with this invention. Such dimer agonists can include 'monomeric' units which exhibit agonist or antagonist activity for the related receptor molecule and may be the same or different. The dimers are preferably small peptides but may alternatively be small molecule pharmacophores. These molecules when dimerized exhibit agonist activity of cell-surface receptors in vitro and in vivo. Such receptors include, for example, EPO, GM-CSF, G-CSF, M-CSF, GH, EGF, PDGF, VEGF, Insulin and FGF. Other receptors which are activated by heterodimerization or multimerization may also be subject to activation by this mechanism including, IL-3, IL-5, IL-6, IL-2 and TPO. The dimers of the present invention have two 'monomeric' peptide units of 10 to 40 or more amino acids, preferably 14 to about 20 amino acid residues in length. In a preferred embodiment, these monomeric peptide units comprise a core sequence of amino acids $X_3X_4X_5GPX_6TWX_7X_8$ (SEQ ID NO: 1) where each amino acid is indicated by standard one letter abbreviation; $X_3$ can be C, A, α-amino-γ-bromobutyric acid, or Hoc, where Hoc is homocysteine; $X_4$ can be R, H, L, or W; $X_5$ can be M, F, or I; $X_6$ is independently selected from any one of the 20 genetically coded L-amino acids or the stereoisomeric D-amino acids; $X_7$ can be D, E, I, L, or V; and $X_8$ can be C, A, α-amino-γ-bromobutyric acid, or Hoc, where Hoc is homocysteine, provided that either $X_3$ or $X_8$ is C or Hoc. Preferably, the monomeric peptide unit of the dimer comprises a core sequence $YX_2X_3X_4X_5GPX_6TWX_7X_8$ (SEQ ID NO: 2) where each amino acid is indicated by standard one letter abbreviation; each $X_2$ and $X_6$ is independently selected from any one of the 20 genetically coded L-amino acids; $X_3$ can be C, A, α-amino-γ-bromobutyric acid, or Hoc, where Hoc is homocysteine; $X_4$ can be R, H, L, or W; $X_5$ can be M, F, or I; $X_7$ can be D, E, I, L, or V; and $X_8$ can be C, A, α-amino-γ-bromobutyric acid, or Hoc, where Hoc is homocysteine, provided that either $X_3$ or $X_8$ is C or Hoc.

More preferably, the monomeric peptide unit of the dimer comprises a core sequence of amino acids $X_1YX_2X_3X_4X_5GPX_6TWX_7X_8X_9X_{10}X_{11}$ (SEQ ID NO: 3), where each amino acid is indicated by standard one letter abbreviation; each $X_1$, $X_2$, $X_6$, $X_9$, $X_{10}$, and $X_{11}$ is independently selected from any one of the 20 genetically coded L-amino acids; $X_3$ can be C, A, α-amino-γ-bromobutyric acid, or Hoc, where Hoc is homocysteine; $X_4$ can be R, H, L, or W; $X_5$ can be M, F, or I; $X_7$ can be D, E, I, L or V; and $X_8$ can be C, A, α-amino-γ-bromobutyric acid, or Hoc, where Hoc is homocysteine, provided that either $X_3$ or $X_8$ is C or Hoc.

In a more preferred embodiment, both $X_3$ and $X_8$ will be C and thus, the monomeric peptide unit of the dimer comprises a core sequence of amino acids $X_1YX_2CX_4X_5GPX_6TWX_7CX_9X_{10}X_{11}$ (SEQ ID NO: 4). More preferably, the monomeric peptide unit comprises a core sequence of amino acids $X_1YX_2CX_4X_5GPX_6TWX_7CX_9X_{10}X_{11}$ (SEQ ID NO: 5), where $X_4$ can be R or H; $X_5$ can be F or M; $X_6$ can be I, L, T, M, or V; $X_7$ is D or V; $X_9$ can be G, K, L, Q, R, S, or T; and $X_{10}$ can be A, G, P, R, or Y. In a most preferred embodiment, the monomeric peptide unit of the dimer comprises a core sequence of amino acids $X_1YX_2CX_4X_5GPX_6TWX_7CX_9X_{10}X_{11}$ (SEQ ID NO: 6), where $X_1$ can be D, E, L, N, S, T, or V; $X_2$ can be A, H, K, L, M, S, or T; $X_4$ is R or H; $X_9$ can be K, R, S, or T; and $X_{10}$ is P. Particularly preferred monomeric peptide units of the present dimers include:

GGLYLCRFGPVTWDCGYKGG (SEQ ID NO: 7);
GGTYSCHFGPLTWVCKPQGG (SEQ ID NO: 8);
GGDYHCRMGPLTWVCKPLGG (SEQ ID NO: 9);
VGNYMCHFGPITWVCRPGGG (SEQ ID NO: 10);
GGVYACRMGPITWVCSPLGG (SEQ ID NO: 11);
VGNYMAHMGPITWVCRPGG (SEQ ID NO: 12);
GGTYSCHFGPLTWVCKPQ (SEQ ID NO: 13);
GGLYACHMGPMTWVCQPLRG (SEQ ID NO: 14);
TIAQYICYMGPETWECRPSPKA (SEQ ID NO: 15);
YSCHFGPLTWVCK (SEQ ID NO: 16);
YCHFGPLTWVC (SEQ ID NO: 17); and
SCHFGPLTWVCK (SEQ ID NO: 18).

The dimer peptides of the present invention exhibit increased biological potency in vitro and in vivo relative to the monomeric agonists from which the dimers are derived. Moreover, cell surface receptor antagonists can be 'converted' to cell surface receptor agonists in accordance with the present invention. Specifically, a cell surface receptor antagonist can be dimerized with PEG or another appropriate linker which permits mutual binding of the monomeric moieties with the receptors. As a result, the dimer exhibits effective binding to the target receptor and behaves as an agonist. Accordingly, the dimers of this invention demonstrate enhanced biological potency in vitro and in vivo relative to their monomeric forms.

The dimer peptides of the present invention bind to and biologically activate the cell surface receptor or otherwise behave as agonists and are preferably formed by employing polyethylene glycol as a linker between the monomeric peptide units described herein. While other conventional chemical systems can also be employed to form the dimer peptides of this invention including using other known polymeric compounds, pegylation is preferred.

The linking compounds of the present invention include any molecule which covalently binds the monomeric peptides at an appropriate distance or which otherwise effects dimerization of the particular cell surface receptor thereby initiating biological efficacy.

Starting with an appropriate synthetic peptide, containing a free amino group or other reactive site such as hydroxyls, carboxylic acids or sulfhydryls, the peptide is added in excess to a reaction mixture containing a corresponding reactive polymer. The polymer can be of a repeating nature such as polyethylene glycol, peptides, modified peptides or peptide analogs. Alternatively, the peptide can be dimerized on a small molecule scaffold such as activated benodiazepins, oxazolones, azalactones, aminimides or diketopiperazines. The most readily available linker of variable distance are ones based on linear unbranched polyethylene glycols.

The following is a schematic of a preferred preparatory methodology employing PEG succinimidyl propionate as the linker between the monomer units of the dimer peptides.

Scheme 1.

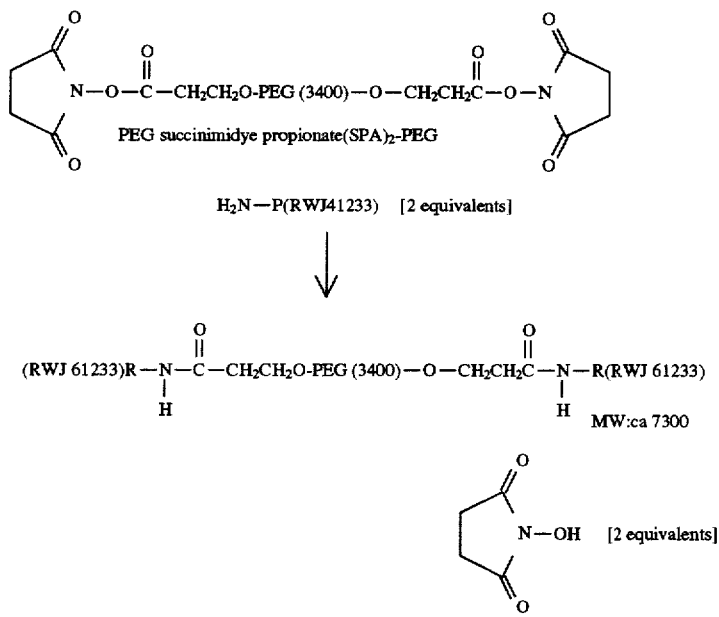

Dimerization and especially pegylation in a head-to-head (amino to amino terminus) or head-to-tail (amino to carboxyl terminus) configuration is preferred relative to internal covalent binding of the monomeric peptides. The 'monomer' units of the dimer peptides of the present invention can be the same or different, although the same are preferred.

The monomeric peptides which are used to form the dimers of the present invention can be prepared by classical chemical methods well known in the art. The standard methods include, for example, exclusive solid phase synthesis and recombinant DNA technology. See, e.g. Merrifield (1963) *J. Am. Chem. Soc.* 85:2149. Solid phase synthesis is typically commenced from the C-terminal end of the peptide using an α-amino protected resin. A suitable starting material can be prepared by attaching the required α-amino acid to a chloromethylated resin (such as BIO-BEADS SX-1, Bio Rad Laboratories, Richmond, Calif.), a hydroxymethyl resin, (described by Bodonszky et al. (1966) *Chem. Ind.* (London) 38:1597) or a benzhydrylamine resin (described by Pietta and Marshall (1970) *Chem. Commn.* 650).

The α-amino protecting groups are those known to be useful in the art of stepwise synthesis or peptides. Included are acyl type protecting groups (e.g. formyl, trifluoroacetyl, acetyl), aromatic urethane type protecting groups (e.g. benzyloxycarboyl (Cbz) and substituted Cbz), aliphatic urethane protecting groups (e.g.. t-butyloxycarbonyl (Boc), isopropyloxycarbonyl, cyclohexyloxycarbonyl) and alkyl type protecting groups (e.g., benzyl and triphenylmethyl). The preferred X-amino protecting group is Fmoc. The side chain protecting group (typically ethers, esters, trityl, PMC, and the like) remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, Z-Br-Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting groups for Thr and Ser are benzyl. The side chain protecting groups for Arg include nitro, Tosy. (Tos), Cbz, adamantyloxycarbonyl mesitoylsulfonyl (Mts), or Boc. The side chain protecting groups for Lys include Cbz, 2-chlorobenzyloxycarbonyl (2-Cl-Cbz), 2-bromobenzyloxycarbonyl (2-BrCbz), Tos, or Boc.

After removal of the α-amino protecting group, the remaining protected amino acids are coupled stepwise in the desired order. Each protected amino acid is generally reacted in about a 3-fold excess using an appropriate carboxyl group activator such as 2-(1H-benxotriazol-1-yl)-1,1,3,3tetramethyluronium hexafluorophosphate (HBTU) or dicyclohexylcarbodiimide (DCC) in solution of methylene chloride ($CH_2Cl_2$), or dimethyl formamide (DMF) mixtures.

After the desired amino acid sequence has been completed, the desired peptide is decoupled from the resin support by treating the mixture with a reagent such as trifluoroacetic acid (TFA) or hydrogen fluoride (HF). These reagents not only cleave the peptide from the resin, but also cleave all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These procedures can also be used to synthesize peptides in which amino acids other than the 20 naturally occurring, genetically encoded amino acids are substituted at one, two or more positions of any of the compounds of the invention.

For instance, naphthylalanine can be substituted for tryptophan, facilitating synthesis. Other synthetic amino acids that can be substituted into the peptides of the present invention include L-hydroxypropyl, L-3,4-dehydroxyphenylalanyl, δ amino acids such as L-δ-hydroxylysyl and D-δ-methylalanyl, L-α-methylalanyl, β amino acids, and isoquinolyl. D-amino acids and non-naturally occurring synthetic amino acids can also be incorporated into the peptides of the present invention.

In another embodiment of the present invention, a method of enhancing the in vitro or in vivo biological potency of a cell surface receptor agonist is provided. This methodology is achieved by dimerizing the receptor agonist with a linker molecule, such as PEG, to form an appropriate spatial relationship between the monomeric peptide units of the dimer and thereby permitting each of the constituents of the dimers to bind to their receptors to achieve enhanced biological potency, i.e., to dimerize and thereby activate the receptors to induce the relevant biological activity of the particular cell-surface receptor, e.g. EPO-R. Biological activity can be measured by the skilled artisan in various in vitro and in vivo assays and as demonstrated in the examples of the present invention.

The peptide or molecule with binding affinity for a given receptor will have increased conformational flexibility leading to fewer barriers to effective receptor interaction and subsequently receptor activation. This is also indicated for molecules which can bind but not activate a receptor subtype in that such molecules can become more effective inhibitors of ligand binding.

The present invention further provides a method for altering a cell-surface receptor antagonist, a molecule exhibiting receptor binding but no biological activity, to behave as a cell-surface receptor agonist in vitro or in vivo. This method is achieved by dimerizing the antagonist molecule with an appropriate linker molecule such as PEG, other polymerized molecules or a peptide. In a preferred embodiment, an EPO antagonist, i.e. a peptide exhibiting receptor binding but no biological EPO activity can be altered by dimerization to obtain a dimer which behaves as an EPO receptor agonist. Thus, for example, in the case of EPO-R these include the monomeric peptide units of the present dimers comprising a core sequence of general formula $(X_0X_2)_nX_3X_4X_5GPX_6TWX_7X_8$ (SEQ ID NO: 19) wherein $X_2$ through $X_8$, are as previously defined herein, in (SEQ ID NO: 2), n is 1 or 0 and $X_0$ is any one of the naturally occurring L-amino acids except Y (tyrosine); n is defined herein as the number of occurrences of $(X_0X_2)$ which can be 1 or none in the core sequence. When $X_2$ is present, i.e., when n=1, $X_0$ is not tyrosine and $X_0$ is not any non-naturally occurring aromatic amino acid analog. Such monomeric peptide units of the dimers of this invention can be prepared by truncating the peptides of FIG. 9, for example, from the N-terminus to delete the Y, tyrosine residue in SEQ ID NOS. 21–93. Such monomeric peptides can also be prepared by substitution of Y in the peptides of FIG. 9.

These molecules, demonstrate only binding activity in their 'monomeric' form, but exhibit agonist activity after dimerization with a linking compound such as PEG. Accordingly, the present method comprises identifying a monomeric peptide as herein defined which does not demonstrate biological activity and dimerizing that antagonist in accordance with the present invention to obtain a cell-surface-receptor agonist i.e., in dimeric form. Contacting the appropriate cell-surface receptor with the thus formed dimer activates, i.e. dimerizes such receptors and thus induces biological activity of the receptor. Such monomeric units as shown in FIG. 9 can be truncated from the N-terminus such as SCHFGPLTWVCK (SEQ ID NO: 18) to eliminate the tyrosine residue at position $X_0$ of the formula $(X_0X_2)_nX_3X_4X_5GPX_6TWX_7X_8$ (SEQ ID NO: 19) or merely substituted with any of the remaining 19 naturally occurring amino acids or with other than a non-naturally occurring aromatic amino acid analog. In accordance with the present invention it has been determined that the tyrosine residue at position $X_0$ of the foregoing formula is critical to biological activity of the monomer peptide. Deletion or substitution of the tyrosine eliminates biological activity. When dimerized however the entity exhibits enhanced biological activity.

For example, tyrosine (Y) substituted in the formula $YX_2X_3X_4X_5GPX_7X_8$ (SEQ ID NO: 2) by p-iodohydroxyphenylalanine, p-fluorohydroxyphenylalanine, p-amino-hydroxyphenylalanine act as EPO-R monomer agonists but substitution with threonine or alanine for tyrosine at position Y causes the monomer peptide to act as an EPO-R antagonist. However, when dimerized in accordance with the present invention, such dimers behave as EPO-R agonists. The monomeric peptide units identified at FIG. 9, for example, behave as EPO-R antagonists in the absence of tyrosine at position Y of the formula above. When such antagonists are dimerzied, the dimer behaves as an EPO-R agonist.

In a further embodiment of the present invention, pharmaceutical compositions comprising at least one of the dimers of this invention can be employed to therapeutically treat disorders resulting from deficiencies of biological factors such as EPO, GH, GM-CSF, G-CSF, EGF, PDGF, VEGF, insulin, FGF and the like. These pharmaceutical compositions may contain buffers, salts and other excipients to stabilize the composition or assist in the delivery of the dimerized molecules.

In a preferred embodiment, the present invention provides a method for treating disorders associated with a deficiency of EPO. The method is accomplished by administering at least one of the dimers identified herein for a time and under conditions sufficient to alleviate the symptoms of the disorder, i.e. sufficient to effect dimerization or biological activation of EPO receptors. In the case of EPO such methodology is useful in the treatment of end-stage renal failure/dialysis; anemia, especially associated with AIDS or chronic inflammatory diseases such as rheumatoid arthritis and chronic bowel inflammation; auto-immune disease; and for boosting the red blood cell count of patient when necessary, e.g. prior to surgery or as pretreatment to transfusion. The dimers of the present invention which behave as EPO agonists can be used to activate megakaryocytes.

Since EPO has been shown to have a mitogenic and chemotactic effect on vascular endothelial cells as well as an effect on central cholinergic neurons (see, e.g., Amagnostou et al. (1990) Proc. Natl. Acad. Sci. USA 87:597805982 and Konishi et al. (1993) Brain Res. 609:29–35), the compounds of this invention can also be used to treat a variety of vascular disorders, such as promoting wound healing, growth of collateral coronary blood vessels (such as those that may occur after myocardial infarction), trauma, and post vascular graft treatment, and a variety of neurological disorders, generally characterized by low absolute levels of acetyl choline or low relative levels of acetyl choline as compared to other neuroactive substances e.g., neurotransmitters.

Accordingly, the present invention includes pharmaceutical compositions comprising, as an active ingredient, at least one of the peptide dimers of the present invention in association with a pharmaceutical carrier or diluent. The dimers of this invention can be administered by oral, parenteral (intramuscular, intraperitoneal, intravenous (IV) or subcutaneous injection), transdermal (either passively or using iontophoresis or electroporation) or transmucosal (nasal, vaginal, rectal, or sublingual) routes of administration in dosage forms appropriate for each route of administration.

Solid dosage forms for oral administration include capsules, tablets, pill, powders, and granules. In such solid dosage forms, the active compound is admixed with at least one inert pharmaceutically acceptable carrier such as sucrose, lactose, or starch. Such dosage forms can also comprise, as it normal practice, additional substances other than inert diluents, e.g., lubricating, agents such as magnesium stearate. In the case of capsules, tablets and pills, the dosage forms may also comprise buffering, agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally dosage levels of between 0.001 to 10 mg/kg of body weight daily are administered to mammals.

As can be appreciated from the disclosure above, the present invention has a wide variety of applications. Accordingly, the following examples are offered by way of illustration, not by way of limitation.

EXAMPLE 1

SDS-PAGE gels (10–20% gradient SDS-PAG plates, 84×70×1.0 mm, Integrated Separation Systems, Natick, Mass.) were stained with Coomasie Brilliant Blue R-250 (BioRad). A commercial preparation of activated difunctional polyethylene glycol (PEG-succinimidylpropionate, SPA2, MW ca. 3400) was purchased from Shearwater Polymers, Huntsville, Ala. as was the monofunctional reagent, methoxy-PEG-succinimidylproprionate, MW ca 5000. Peptide (SEQ ID NO: 8) and all other peptides were obtained from the Peptide Synthesis Facility RWJ-PRI, La Jolla, Calif. or Quality Controlled Biochemical, Hopkinton Mass. These peptides were cyclized via oxidation of their intramolecular cysteines, amidated at the C-terminus and mass confirmed by FAB-MS. All were Ellman Reaction negative. Tris base was obtained from BioRad, Hercules, Calif. (DPDPB) and trifluoracetic acid (HPLC grade) were obtained from Pierce Chemical Co., Rockford Ill.

Mono-PEG Conjugation of Peptide
GGTYSCHFGPLTWVCKPQGG (SEQ ID NO: 8)

This example describes the preparation of mono-PEG conjugates of peptide (SEQ ID NO: 8), using the monofunctional amine reactive polymer analog m-SPA-PEG to be used as a control in experiments described herein. The reaction was carried out with polymer in excess (ca. 3 fold) by resuspending 142.5 mg (0.0286 mmol, MW ca. 5000) of polymer in 4 ml PBS at pH 7.5 and adding 20 mg peptide (SEQ ID NO: 8) (0.0095 mmol, MW 2092) dissolved in 1 ml of 0.1% trifluoroacetic acid. The mixture was incubated on ice for 20 hours. The reaction was subsequently adjusted to a final concentration 50 mM Tris by the addition of 1M tris-HCl at pH 7.5. The reaction mixture was incubated on ice for one hour. Analytical HPLC suggested that there were two main reaction products of essentially equivalent magnitude which were not baseline resolved. Preparative HPLC (using the flatter gradient system described in Example 8) and conservative cuts resulted in collection of two product peaks eluting at ca 44 and 47 minutes. After lyophilization, 24.8 mg, 16.5 mg of each species was recovered, respectively. Mass spectral analysis of these two species demonstrated centroid masses of 7092 (peak 1) and 12036 (peak 2) indicating the coupling of one or two PEG molecules, respectively, to the peptide (Table I).

Tris Inactivated Polymer

Tris inactivated polymer was formed by incubation of 5 mM SPA2 polymer dissolved in PBS (Gibco, Gaithersburg, Md.) with 50 mM tris-HCl, pH 7.5 added and used without further purification.

TABLE 1

Recovery Yield of Peptide Conjugation Reaction and Apparent Molecular Mass of Product

| SEQ. I.D. No. | Sequence | Mass | Conjugation Reagent | Main Product Mass (centroid m/z) | Yield (% of theoretical) |
|---|---|---|---|---|---|
| 8 | GGTYSCHFGPLTWVCKPQGG | 2092 | SPA2-PEG (MW ca. 3400) | 7834 | 69 |
|   |   |   | m-SPA-PEG (MW ca. 5000) | 7092 (peak 1) | — |
|   |   |   |   | 12036 (peak 2) | — |
| 13 | GGTYSCHFGPLTWVCKPQ | 1978 | SPA2-PEG | 7560 | 54 |
| 20 | Ac-GGTYSCHFGPLTWVCKPQGG | 2133 | SPA2-PEG | 7862 | 30 |
| 14 | GGLYACHMGPMTWVCQPLRG | 2177 | SPA2-PEG | 7872 | 37 |
| 18 | SCHFGPLTWVCK | 1375 | SPA2-PEG | 6326 | 45 |

13

EXAMPLE 2

PEG Dimerization of Peptide GGTYSCHFGPLTWVCKPQGG (SEQ ID NO: 8) (lot #1)

Examples 2–7 describe the dimerization of various peptides described by the present invention. The modification of peptide (SEQ ID NO: 8) was carried out by resuspending 25 mg (0.0071 mmol) of polymer in 4 ml PBS at pH 7.5, and adding a 3 fold molar excess of peptide (SEQ ID NO: 8) (0.0213 mmol, 44.5 mg, MW 2092) dissolved in 1 ml of 0.1% trifluoroacetic acid. The mixture was incubated on ice. After 3 hours of incubation, an additional 7.5 mg (0.0036 mmol) of lyophilized peptide was added, resulting in a final ratio of 3.5 moles of peptide per each mole of SPA2. The mixture was incubated an additional 17 hours on ice. The reaction mixture was adjusted to a final concentration of 50 mM Tris by the addition of 1M tris-HCl of pH 7.5 and incubated on ice for 1 hour. The sample was subjected to analytical and preparative HPLC as described in Example 8. After preparative HPLC and lyophilization, 38 mg of PEG dimer was recovered. The theoretical yield for this experiment was 55 mg based on a calculated mass of 7600 mg/mmol for a yield of 69% (Table I).

EXAMPLE 3

PEG Dimerization of Peptide GGTYSCHFGPLTWVCKPQGG (SEQ ID NO: 8) (lot #2)

The modification of peptide (SEQ ID NO: 8) was carried out by resuspending 25 mg (0.0071 mmol) of polymer in 4 ml PBS at pH 7.5, and adding a ca. 3 fold molar excess of peptide (SEQ ID NO: 8) (0.0213 mmol, 45.8 mg, MW 2092) dissolved in 1 ml of 0.1% trifluoroacetic acid. The mixture was incubated on ice for 22 hours. At that time, the reaction was adjusted to a final concentration of 50 mM Tris by the addition of 1M tris-HCl, pH 7.5. The reaction mixture was incubated on ice for 1 hour. The sample was subjected to analytical and preparative HPLC as described in Example 8. After preparative HPLC and lyophilization, 37 mg of PEG dimer was recovered. The theoretical yield for this experiment was 55 mg based on a calculated mass of 7600 mg/mmol for a yield of 68% (Table I).

EXAMPLE 4

PEG Dimerization of Peptide GGTYSCHFGPLTWVCKPQ (SEQ ID NO: 13)

The modification of peptide (SEQ ID NO: 13) was carried out by resuspending 11.2 mg (0.0033 mmol) of polymer in 2.5 ml PBS at pH 7.5, and adding a ca. 3 fold molar excess of peptide (SEQ ID NO: 13) (0.010 mmol, 20 mg, MW 1978) dissolved in 0.25 ml of 0.1% trifluoroacetic acid. The mixture was incubated on ice for 20 hours. At that time, 0.25 ml of 1M tris-HCl at pH 7.5 was added. The reaction mixture was incubated at 4° C. for one hour. The sample was subjected to analytical and preparative HPLC as described in Example 8. The main preparative reaction product peak eluted at ca 43 minutes. After preparative HPLC and lyophilization, 13.3 mg of PEG dimer was recovered. The theoretical yield for this experiment was 24.42 mg based on a calculated mass of 7400 mg/mmol for a yield of 54% (Table I).

EXAMPLE 5

PEG Dimerization of Peptide Ac-GGTYSCHFGPLTWVCKPQGG (SEQ ID NO: 20)

The modification of peptide (SEQ ID NO: 20) was carried out by resuspending 10.5 mg (0.0031 mmol) of polymer in 2.5 ml PBS at pH 7.5, and adding a ca. 3 fold molar excess of peptide (SEQ ID NO: 20) (0.0094 mmol, 20 mg, MW 2133) dissolved in 0.25 ml of 0.1% trifluoroacetic acid and the mixture incubated at 4° C. for 28 hours. At that time, the reaction as monitored by HPLC was estimated to be approximately 30% complete, the temperature was shifted to ambient and an additional 27 hour incubation provided no net increase in product. Because of possible hydrolysis of the reactive polymer, an additional 5 mg of polymer was added and the incubation was continued for an additional 16 hours. At that time, 0.25 ml of 1M tris-HCl, pH 7.5 was added and the reaction mix was incubated at 4° C. for an additional 1 hour. The sample was subjected to analytical and preparative HPLC using a flatter gradient system as described in Example 8. The main preparative reaction product peak eluting at ca 48 minutes. After preparative HPLC and lyophilization, 10.4 mg of PEG dimer was recovered. The theoretical yield for this experiment was 34.4 mg based on a calculated mass of 7650 mg/mmol for a yield of 30% (Table I).

EXAMPLE 6

PEG Dimerization of Peptide (SEQ ID NO: 14)

The modification of peptide (SEQ ID NO: 14) was carried out by resuspending 2.6 mg (0.00076 mmol) of polymer in 3.0 ml PBS at pH 7.5 and adding a ca. 3 fold molar excess of peptide (SEQ ID NO: 14) (0.00229 mmol, 5 mg, MW 2177) dissolved in 0.1 ml of 0.1% trifluoroacetic acid. The mixture was incubated on ice for 26 hours. At that time, 0.25 ml of 1M-tris-HCl at pH 7.5 was added. The reaction mixture was incubated at 4° C. for 1 hour. The sample was subjected to analytical and preparative HPLC using the flatter gradient system described in Example 8. The main preparative reaction product peak eluted at ca 46 minutes. After preparative HPLC and lyophilization, 2.2 mg of PEG dimer was recovered. The theoretical yield for this experiment was 24.42 mg based on a calculated mass of 7400 mg/mmol for a yield of 37% (Table I).

EXAMPLE 7

PEG Dimerization of Peptide (SEQ ID NO: 18)

The modification of peptide (SEQ ID NO: 18) was carried out by resuspending 1.2 mg (0.00036 mmol) of polymer in 0.5 ml PBS at pH 7.5, and adding a ca. 3 fold molar excess of the peptide (0.0011 mmol, 1.5 mg, MW 2177) dissolved in 0.05 ml of 0.1% trifluoroacetic acid. The mixture was incubated on ice for 20 hours. At that time, 0.1 ml of 1M tris-HCl at pH 7.5 was added. The reaction mixture was incubated at 4° C. for 1 hour. The sample was subjected to purification using an analytical HPLC system as described in Example 8. The main reaction product peak eluted at ca 38 minutes. After preparative HPLC and lyophilization, 1 mg of PEG dimer was recovered. The theoretical yield for this experiment was 2.2 mg based on a calculated mass of 6150 mg/mmol for a yield of 45% (Table I).

EXAMPLE 8

Analytical and Preparative HPLC Analysis

The accumulation of the dimers described above in Examples 1–7 was monitored by analytical reverse phase HPLC. The analysis was carried out using a Vydac C-18 Protein-Peptide column (0.46×25 cm, part no. 218TP54) and a Rainin Gradient HPLC system fitted with a Dynamax dual wavelength detector. At injection, the column was equilibrated in 0.1% TFA in dH$_2$O and was developed with a 45 minute linear gradient (0–100%) of acetonitrile (ACN) containing 0.1% TFA beginning at 10 minutes after injection. The flow rate was held constant at 1 ml/min. Under these analytical conditions, the SPA2 polymer and tris inactivated polymer did not appear to bind the column while a major reaction product with a retention time (37 minutes) was identified (FIG. 1). Peptide (SEQ ID NO: 8) demonstrated a retention time of 35 minutes and the excess peptide utilized in the reaction was clearly distinguished from the nascent reaction products.

Figure 2:
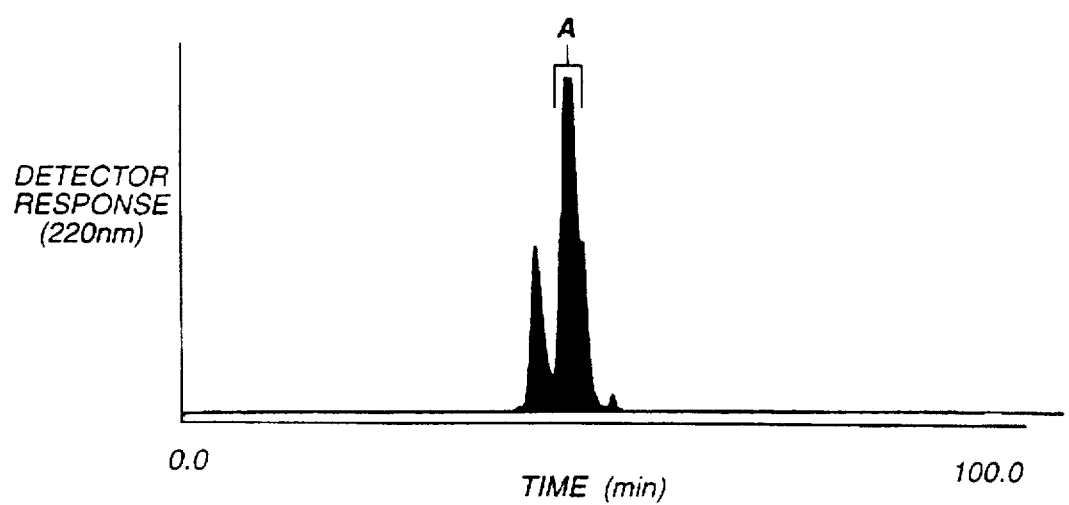
FIG. 2 shows a major peak, with a retention time of 48 minutes, following purification of the dimerized EPO peptide, (SEQ ID NO: 8).

The main product reaction product peak was purified by preparative reverse phase HPLC on the same chromatographic system using a Vydac C-18 Protein-Peptide column (2.2×25 cm, part no. 218TP15022). Injection of the reaction mix (6 ml) occurred with the column equilibrated at 80:20, H$_2$O:ACN (both containing 0.1% TFA) at a constant flow rate of 8 ml/min. After a 20 minute wash, the column was developed by application of a linear gradient of 100% ACN/0/1% TFA over 60 minutes. The major product peak eluting at 48 minutes was collected and lyophilized (FIG. 2). These elution conditions were subsequently modified to improve the resolution of some conjugation products peptide (SEQ ID NO: 20), mPEG-peptide (SEQ ID NO: 8), peptide (SEQ ID NO: 14) from reaction by products. This was accomplished by application of a flatter linear gradient of 20–80% B over 60 minutes. The variation in retention time due to different peptides and elution condition is described as part of each synthesis example. The materials recovered from the main product peak from each reaction were subsequently analyzed by analytical reverse phase HPLC, MALDI-TOF mass spectrometry, EPO competitive binding potential and for in vitro bioactivity.

The activated PEG used in these experiments has an approximate molecular weight of 3400 and has amine reactive succinimidyl groups on either end of the difunctional linear polymer. This reactivity was employed to couple two equivalents of peptide (SEQ ID NO: 8) (MW=2092) to the polymer with the concomitant liberation of two succinimidyl moieties resulting in a dimeric product as shown in Scheme I. Peptide (SEQ ID NO: 8) contains two potentially reactive amines, one at the N-terminus of the peptide and one in the side chain of the single lysine within the peptide sequence, so that a number of different connectivities between the two molecules was possible.

Figure 3:
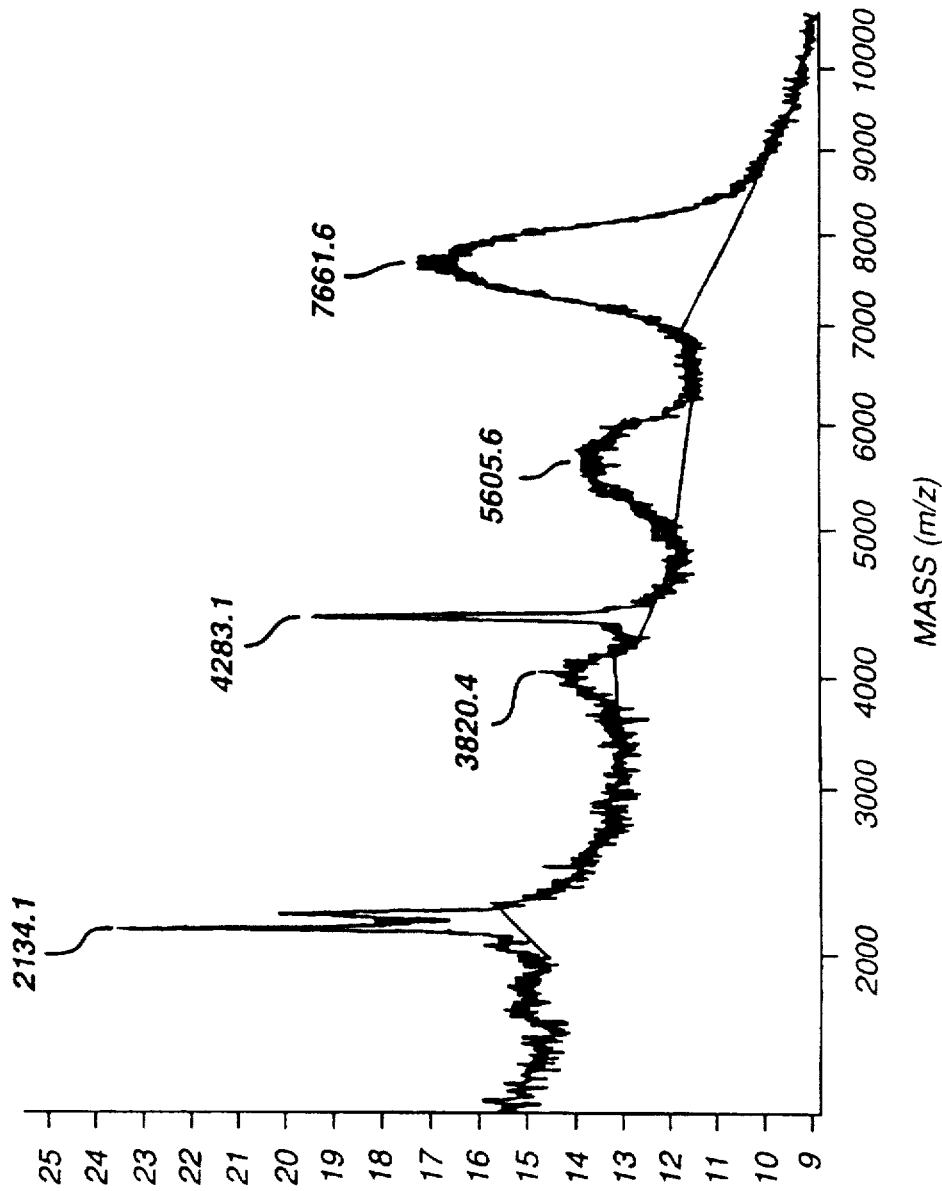
FIG. 3 depicts the MALDI-TOF mass spectral analysis of the dimerized peptides, including peptide (SEQ ID NO: 8), GGTYSCHFGPLTWVCKPQ (SEQ ID NO: 13) and SCHF-GPLTWVCK (SEQ ID NO: 18).
Figure 3C:
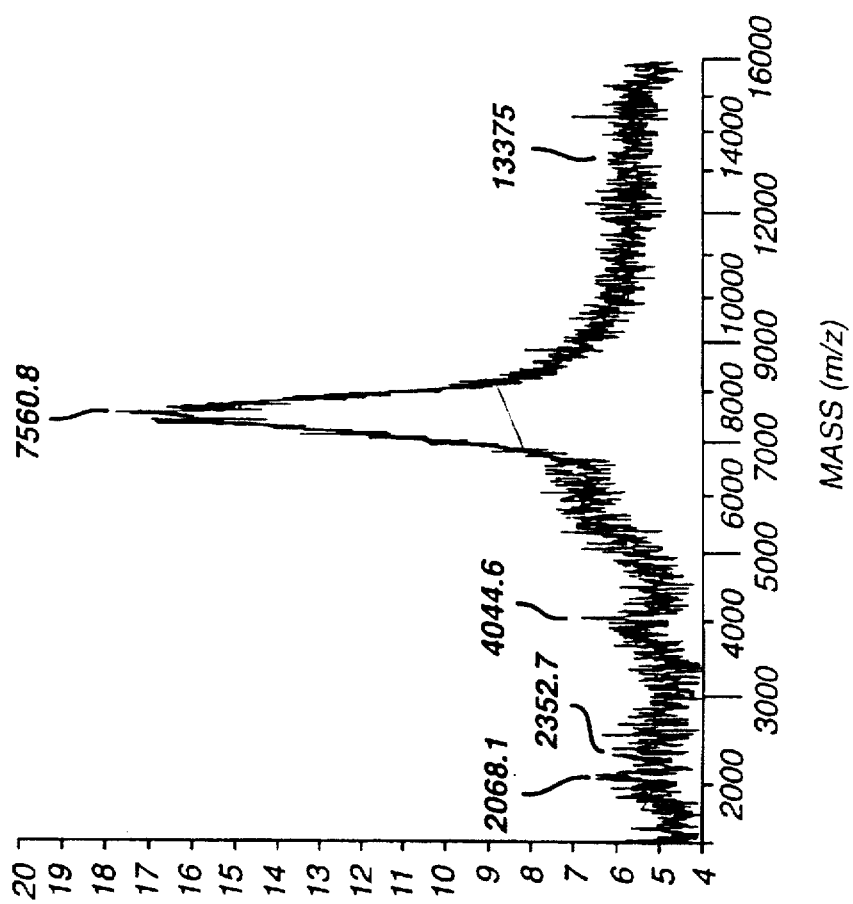
Figure 3D:
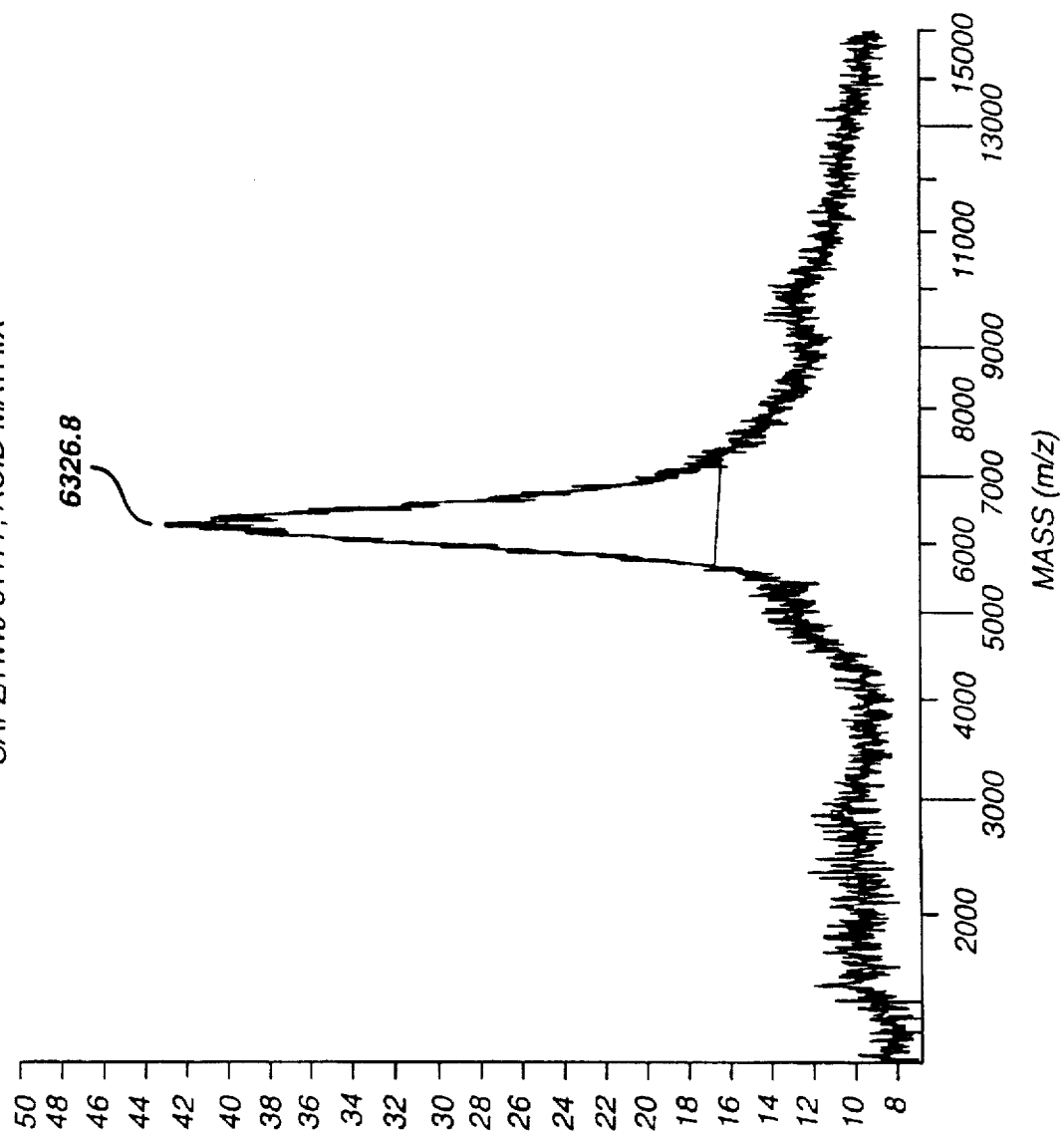

MALDI-TOF mass spectral analysis was supportive of the presence of the expected dimeric product (FIG. 3) as indicated by a predominant species with a centroid mass of 7661. This data shows that the dimeric product described in the present invention was produced using the methods described herein.

EXAMPLE 9

EBP (EPO Binding Protein) Dimerization

This example demonstrates the interaction of peptide (SEQ ID NO: 8), peptide (SEQ ID NO: 16), peptide (SEQ ID NO: 18) and peptide (SEQ ID NO: 13) with EPO binding protein (EBP) using a bifunctional sulphydryl reactive crosslinker, (1,4-Di-[3'-(2'-pyridyldithio)propionamido] butane DPDPB.

Figure 4:
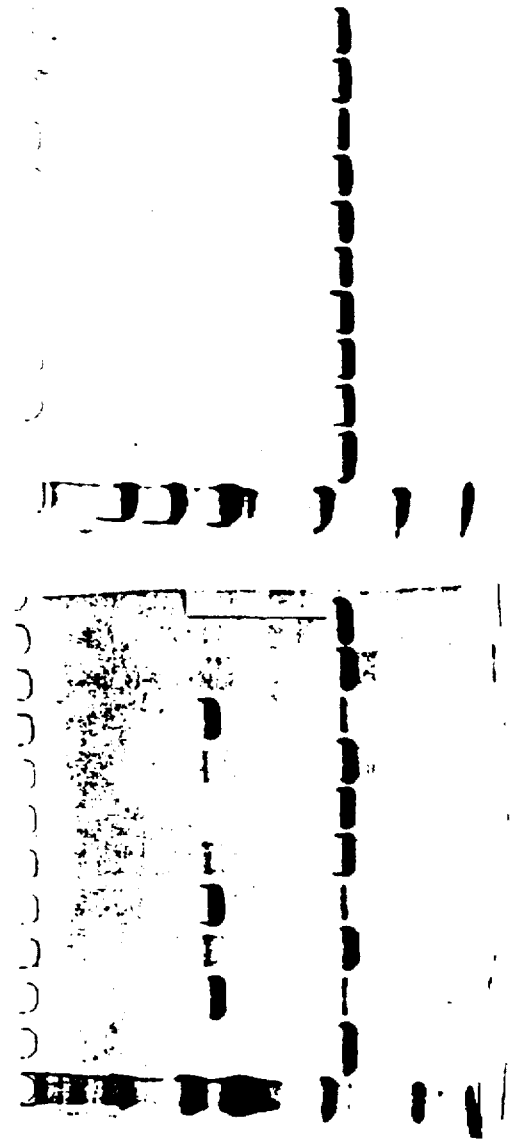
FIG. 4 shows the SDS-PAGE analysis of DPDPB crosslinking of EPO binding protein (EBP) in the presence and absence of EPO agonist peptides.

To explore the interaction of peptide (SEQ ID NO: 8) with EBP, a bifunctional sulphydryl reactive crosslinker (DPDPB) was used in an attempt to stabilize a mimetic dependent dimeric structure. Control experiments demonstrated that the crosslinker does not inactivate the EPO binding potential of EBP or the proliferative properties of peptide (SEQ ID NO: 8). As shown in FIG. 4, a dimeric EBP product was formed by co-incubation of the peptide, peptide (SEQ ID NO: 8), DPDPB and EBP. This data shows the ability of the peptide (SEQ ID NO: 8) to mediate formation of a soluble receptor dimer. To further explore this question, peptides (SEQ ID NO: 13), (SEQ ID NO: 16) and (SEQ ID NO: 18) were examined for their ability to mediate dimerization. As shown in FIG. 4, lanes 7A and 8A, when peptide (SEQ ID NO: 13) was truncated at the carboxyl terminus, it retained good in vitro bioactivity and improved in vivo bioactivity, resulting in a crosslinking signal similar to peptide (SEQ ID NO: 8). However, peptide (SEQ ID NO: 18) did not appear to stabilize the dimerization signal (FIG. 4, lanes 9A and 10A) whereas peptide (SEQ ID NO: 16) (FIG. 4, lanes 5A and 6A) gave a strong dimerization band. These two peptides differ by a single N-terminal tyrosine residue and display a similar profile in the in vitro proliferation assay with peptide (SEQ ID NO: 18) being inactive. Peptide (SEQ ID NO: 16) has an ED$_{50}$ of 3 µM on murine receptor cells. Both peptides have similar IC$_{50}$ values indicating that they both retain binding activity. These results demonstrate that EBP dimerization is a property of the EPO peptide series and that the presence of the tyrosine is critical for this activity and that this corresponds to in vitro bioactivity.

EXAMPLE 10

Immobilized EBP Based [$^{125}$I]EPO Competition Binding Assay

This study examined the binding capacity of the EPO PEG dimers to bind EPO receptors.

The extracellular domain of the human erythropoietin receptor (EPO binding protein, EBP) was expressed and overproduced in *E. coli*. As with many other recombinant eukaryotic proteins produced in *E. coli*, the protein appeared as an insoluble product in laboratory scale fermentations and was refolded and purified to obtain active protein. EPO binding protein produced by this method contains one free sulfhydryl group which can be modified without effecting the solution phase binding of ligand. In order to immobilize the EPO binding protein for equilibrium binding analysis and for competition binding assay, the EPO binding protein was covalently attached to agarose beads.

The iodoacetyl activation chemistry of Sufolink beads (Pierce Chemical Co. Rockford, Ill.) is specific for free thiols and assures that the linkage is not easily reversible. EBP-Sulfolink beads were made as follows: SulfoLink gel suspension (10 ml) was mixed with of coupling buffer (40 ml: 50 mM Tris, pH 8.3, 5 mM EDTA) and the gel was allowed to settle. The supernatant was removed and the EPO binding protein (0.3–1 mg/ml in coupling buffer) to be bound was added directly to the washed beads. The mixture was rocked gently for 30 minutes at room temperature and the beads were allowed to settle for 1 hour at room temperature. The supernatant was removed and retained. The beads were washed twice with 20 ml of coupling buffer. The washes were recovered as well. The beads were then treated with 20 ml of 0.05M cysteine for 30 minutes at room temperature to block unbound sites. Finally, the beads were washed with 50 ml of 1M NaCl, then with 30 ml of PBS, and resuspended in 20 ml of PBS and stored at 4° C. The amount of EBP which was covalently bound to the beads was determined by comparing the OD$_{280}$ of the original EBP solution to the total OD$_{280}$ recovered in the reaction supernatant and the two 20 ml washes. Typically, 40–60% of the applied EBP remains associated with the beads.

Binding assays were initiated by the addition of EPO binding protein beads (50 µl) to individual reaction tubes. Total binding was measured in tubes containing 0.3–30 nM [$^{125}$I]EPO (NEN Research Products, Boston Mass., 100 µCi/µg). For determination of non-specific binding, unlabelled EPO was added at a level of 1000 fold in excess of the corresponding [$^{125}$I]EPO concentration. Each reaction volume was brought to 500 µl with binding buffer (PBS/ 0.2% BSA). The tubes were incubated for five hours (a time period experimentally determined as adequate for the establishment of equilibrium) at room temperature with gentle rocking. After five hours, each reaction mixture was passed through a 1 ml pipet tip plugged with glass wool. The tubes were washed with 1 ml wash buffer (PBS/5% BSA) and this volume as well as 2 additional 1 ml washes were passed through the pipet tip and collected for determination of the free EPO concentration. Equilibrium binding analysis of the specific association of [$^{125}$I]EPO with EPO mimetic binding proteins immobilized on these agarose beads indicates a Kd of 5 nM ±2 based on a linear transformation (Scatchard) of the binding isotherm (FIG. 5).

Competitive binding analysis assays of candidate peptides and dimer peptides were performed as outlined below. Individual peptides were dissolved in DMSO to prepare a stock solution 1 mM. Dimer peptides were contained within PBS at a concentration of 5 mM. All reaction tubes (in duplicate) contained 50 µL of EBP beads, 0.5 nM [$^{125}$I]EPO and 0–500 µM peptide in a total of 500 µL binding buffer.

The final concentration of DMSO was adjusted to 2.5% in all peptide assay tubes. At this concentration DMSO has no detectable effect since an examination of the sensitivity of the assay to DMSO demonstrated that concentrations of up to 25% DMSO (V/V) had no deleterious effect on binding. Non-specific binding was measured in each individual assay by inclusion of tubes containing a large excess of unlabelled EPO (1000 nM). Initial assay points with no added peptide were included in each assay to determine total binding. Binding mixtures were incubated overnight at room temperature with gentle rocking. The beads were then collected using Micro-columns (Isolab, Inc.) and washed with 3 mL of wash buffer. The columns containing the washed beads were placed in 12×75 mm glass tubes and bound radioactivity levels determined in a gamma counter. The amount of bound [$^{125}$I]EPO was expressed as a percentage of the control (total=100%) binding and plotted versus the peptide concentration after correction for non-specific binding. The IC$_{50}$ was defined as the concentration of the analyte which reduced the binding of [$^{125}$I]EPO to the EBP beads by 50%. All data are reported as relative to peptide (SEQ ID NO: 8) which demonstrated an IC$_{50}$ of 5 µM.

Figure 5:
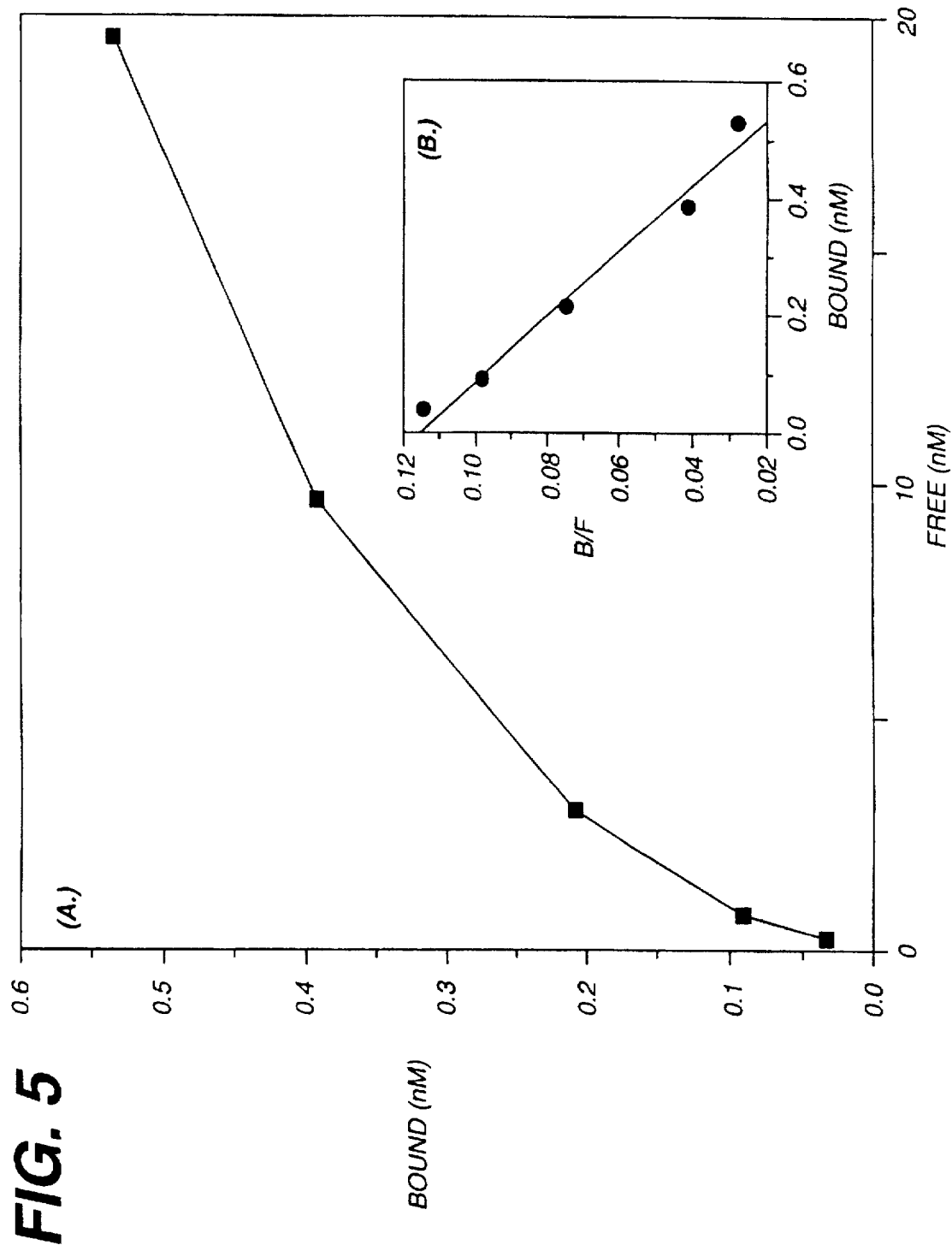
FIG. 5 demonstrates equilibrium EPO binding to immobilized EPO binding protein. Panel A represents the equilibrium binding data and Panel B (inset) is the linear transformation (Scatchard) of the data set in Panel A.
Figure 6:
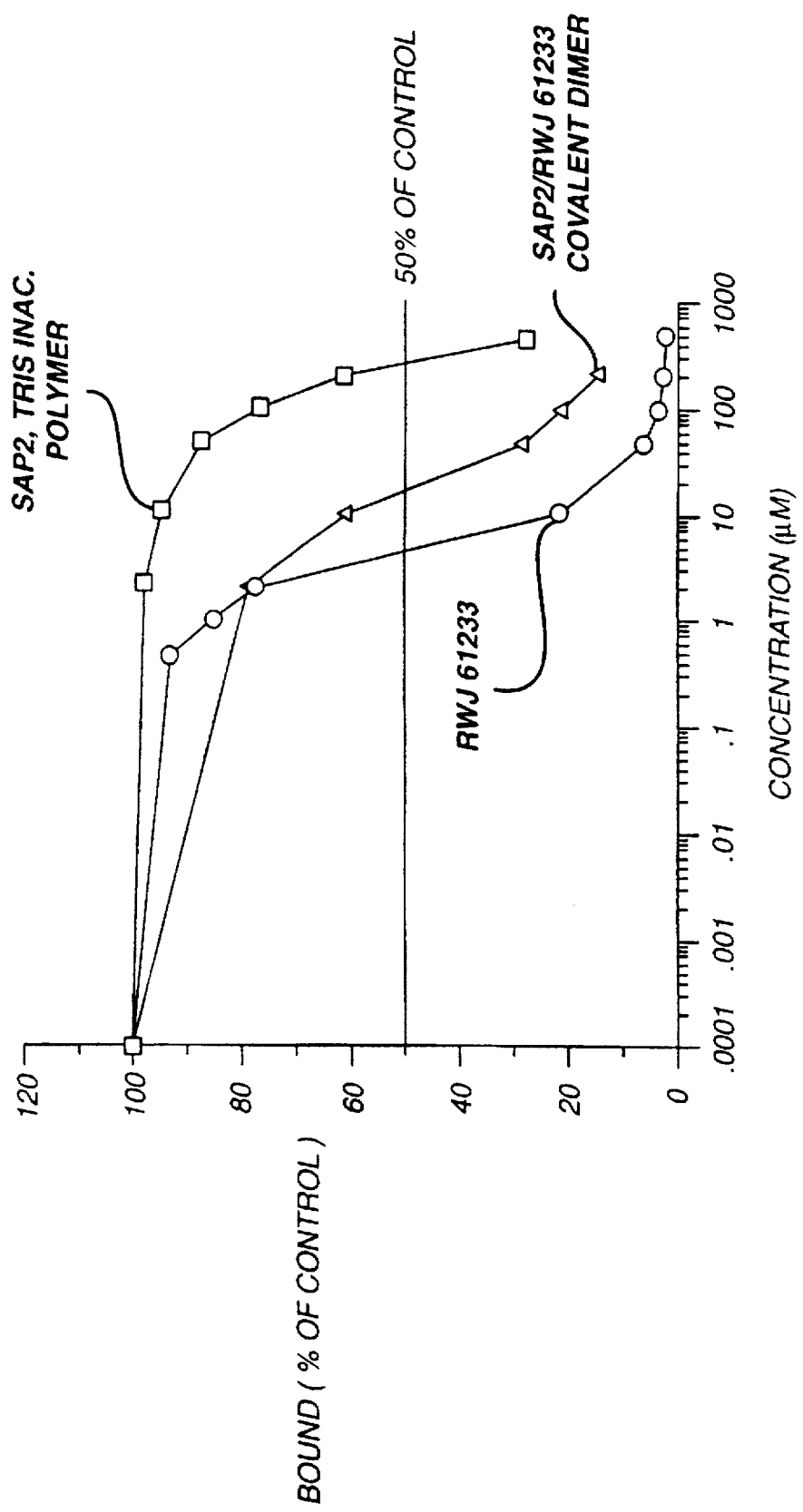
FIG. 6 depicts the results of a competitive binding assay run on the EPO agonist peptide (SEQ ID NO: 8) in competitive binding with [$^{125}$I]EPO to EBP beads (Panel A); and EPO responsive cell proliferation studies in FDC-P1 derived cell lines containing either a human (Panel B) or murine EPO receptor (Panel C).
Figure 6:
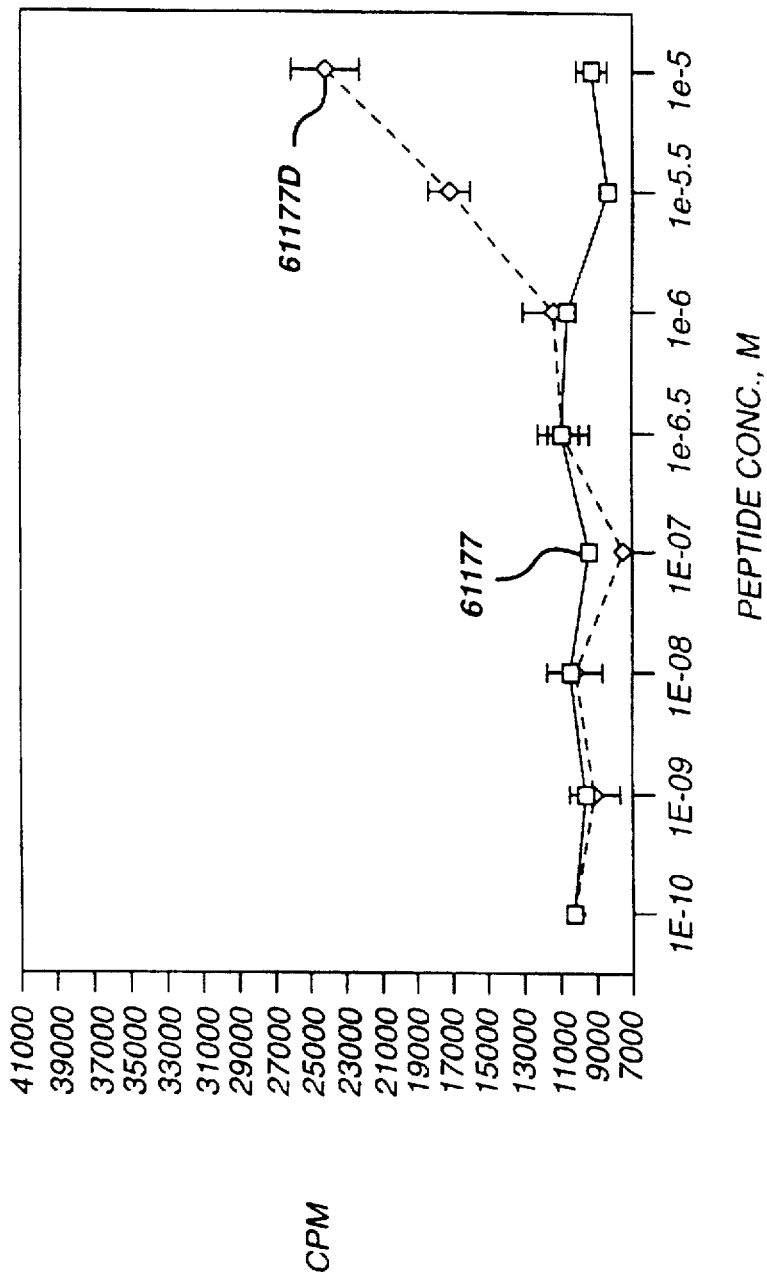

Competitive binding analysis revealed an IC$_{50}$ of 20 µM for the purified dimer, a value four fold greater than peptide (SEQ ID NO: 8) in the same assay (FIG. 5 and Table II). Polymer alone, which was inactivated by treatment with Tris-HCl, demonstrated a detectable competition binding signal but this signal was modest (<10%) at the IC$_{50}$ of the PEG-peptide (SEQ ID NO: 8) dimer.

TABLE II

Table II. Binding and Cell Proliferation Studies

| Compound | Relative Binding[1] | EPO-ED$_{50}$ (µM)* murine receptor | EPO-ED$_{50}$ (µM)* truncated human receptor |
|---|---|---|---|
| Seq. I. D. No. 8 | 1 | 0.1 | 0.09 |
| SAP2, tris inact.polymer | 60 | IA[2] | IA |
| SAP2/Seq. I. D. No. 8 covalent dimer #1 | 4 | 0.01 (10X) | 0.0015 (60X) |
| SAP2/Seq. I. D. No. 8 covalent dimer #2 | 3 | 0.01 (10X) | 0.002 (45X) |
| Seq. I. D. No. 13 | 1.6 | 0.08 | 0.02 |
| SAP2/Seq. I. D. No. 13 covalent dimer | 3 | 0.01 (8X) | 0.002 (10X) |
| Seq. I. D. No. 20 (N-acetyl) | 4 | 0.03 | 0.06 |
| SAP2/Seq. I. D. No. 20 covalent dimer | 12 | 0.2 (–7X) | 0.05 |
| Seq. I. D. No. 14 (terminal NH$_2$) | 0.6 | 0.1 | 0.08 |
| SAP2/Seq. I. D. No. 14 covalent dimer | — | 0.006 (16X) | 0.001 (80X) |

*Amount required to achieve the half maximal level of EPO dependent proliferation (11 pM)
[1] Binding relative to Seq. I. D. No. 8
[2] IA = Inactive
$Note that all peptides are cylic and were analyzed as COOH terminal amides (—CONH$_2$)

EXAMPLE 11

EPO Dependent Cell Proliferation Assays

This example shows the improved potency of PEG-EPO peptide dimers to EPO receptors in human and murine cell lines.

Cell line FDC-P1/ER, an EPO-dependent line expressing the murine EPO receptor, was grown and maintained as described previously (Carroll et al. 1991). Also employed was cell line FDC-P1/trER expressing a functional truncated human EPO receptor (missing the C-terminal 40 amino acids). Both cell lines exhibit EPO dependent cellular proliferation. Briefly, cells were maintained in RPMI 1640 media (Gibco/BRL) containing 10% heat-inactivated fetal calf serum and 10 units/ml of recombinant human EPO. For the cellular proliferation assay, FDC-P1/ER or FDC-P1/trER cells were grown to stationary phase, centrifuged, washed with RPMI 1640 media (no EPO), and plated in EPO minus media for 24 hr.

After 24 hours, the cells were counted, resuspended at 800,000 cells/ml and dispensed at 40,000 cells/well. Stock solutions of the peptide dimer (5 mM in PBS) and peptide (10 mM in DMSO) were prepared and dispensed in triplicate to final concentrations of 1×10$^{-10}$M through 1×10$^{-5}$M and adjusted to a final volume of 0.2 ml. Final DMSO concentrations of 0.1% (V/V, maximal) or less were found to have no cellular toxicity or stimulatory effects. A standard EPO dose response curve was generated with each assay series. After a 42 hr incubation at 37° C. (ca. 2 cell doublings) 1 µCi/well of [$^3$H] thymidine was added and the incubation continued for 6 hr at which time the cells were harvested and counted to assess [$^3$H]thymidine incorporation as a measure of cell proliferation. Results are expressed as the amount of peptide or dimer peptide necessary to yield one half of the maximal activity obtained with recombinant EPO.

As shown in FIG. 5 and Table II, the initial lot of PEG-peptide (SEQ ID NO: 8) dimer demonstrated ED$_{50}$ values of 0.01 µm and 0.0015 µm in EPO responsive cell lines containing the murine or human EPO receptor, respectively. In both cell lines, the parent peptide, peptide (SEQ ID NO: 8), demonstrated an $ED_{50}$ of 0.1 μM, indicating an increase in potency of 10 fold in the murine receptor line and almost 60 fold in the human receptor containing cells. Thus, the dimer was clearly more potent in murine and human lines than the peptides themselves. This was confirmed by generation of a second synthesis lot of PEG-peptide (SEQ ID NO: 8) dimer which resulted in a 10 and 45 fold increase in potency in the murine and human lines, respectively. Polymer alone, which was inactivated by treatment with Tris-HCl, demonstrated no activity in the cell proliferation assay.

A second EPO mimetic peptide, peptide (SEQ ID NO: 13), with the sequence GGTYSCHFGPLTWVCKPQ, was also subjected to a similar PEG dimerization protocol as that described above for peptide (SEQ ID NO: 8). The dimer product of PEG-peptide (SEQ ID NO: 13) is also more active than the unconjugated parent compound (Table II). Both of these dimer peptides have ultimate $ED_{50}$ values near 0.002 μM. In spite of this more modest increase, the experimental evidence clearly indicates that the dimerization of these peptides with PEG results in improved potency.

EXAMPLE 12

To further examine the connectivity of the peptides of the present invention to PEG, peptide molecules, which contained only an internal lysine group were used peptide (SEQ ID NO: 8) analog acetylated at the N-terminus peptide (SEQ ID NO: 20) and a sequence analog peptide (SEQ ID NO: 14) which only had a reactive N-terminal amine were PEG dimerized. In vitro proliferation data of these compounds suggest that potential dimerization through the free amino terminus has the most profound effect on bioactivity giving rise to a species about 80 fold more active than the monomeric parent peptide (SEQ ID NO: 14) dimer. Conjugation through the lysine side chain had no real effect on activity peptide (SEQ ID NO: 20) as did mono-PEG or di-PEG conjugation (Table III). This data indicates that the creation of a head to head dimer (both peptides attached through the N-terminus) using a PEG linker greatly enhances the potency of EPO peptides and approaches a level almost two logs greater than the free parent peptide. Further, this effect was not observed upon simple covalent attachment of linear PEG to peptide (SEQ ID NO: 8) indicating that dimerization is a critical determinant for this increased activity.

TABLE III

Table III. Binding and Cell Proliferation Studies mPEG/

| | | EPO-ED$_{50}$ (μM)* | |
|---|---|---|---|
| Compound | Relative Binding[1] | murine receptor | truncated human receptor |
| Seq. I. D. No. 8 | 1 | 0.1 | 0.09 |
| mPEG/Seq. I. D. No. 8, peak #1 | 60 | 2 | 0.1 |
| mPEG/Seq. I. D. No. 8, peak #2 | >40 | 1 | 0.4 |

*Amount required to achieve the half maximal level of EPO dependent proliferation (11 pM)
[1]ND = Not determined
[2]IA = Inactive
$Binding relative to Seq. I. D. No. 8
Note that all peptides are cyclic and were analysed as COOH terminal amides (—CONH$_2$)

EXAMPLE 13

Polycythemic Exhyposic Mouse Bioassay

This study demonstrates the ability of peptide (SEQ ID NO: 8)/PEG-dimers to retain in vivo bioactivity. Peptides were assayed for in vivo activity in the polycythemic mouse bioassay adapted from the method described by Cotes and Bangham (1961), *Nature* 191: 1065-1067. BDF1 mice were allowed to acclimate to ambient conditions for 7-10 days. Body weights were determined for all animals. Low weight animals (<15 grams) were not used. Mice were introduced to hypobaric chambers with a 24 hour conditioning cycle consisting of 0.40% +/−0.02 atm. for 18 hours followed by 6 hours at ambient pressure for a total of 14 days. Following the 14 day period, mice were placed in ambient pressure for 72 hours prior to dosing. Test samples or recombinant Human Erythropoietin (rHuEPO) standards were diluted in an assay vehicle consisting of Phosphate Buffered Saline (PBS)-0.1% Bovine Serum Albumin (BSA). Peptide sample stock solutions (excluding peptide dimers) were first solubilized in dimethyl sulfoxide (DMSO). Control groups included one group of vehicle alone, and one group of (DMSO) at final concentration of 1%.

Each dose group contained 10 mice. Mice were injected subcutaneously (scruff of neck) with 0.5 ml of the appropriate sample. Forty eight hours following the sample injection, the mice were administered an intraperitoneal injection of 0.2 ml of [$^{59}$Fe] (approximately 18.0 milliCuries/milligram, Dupont, NEN) and 0.75 microCuries/Mouse.

Mouse body weights were determined twenty four hours following [$^{59}$Fe] administration and the mice were sacrificed forty eight hours following the [$^{59}$Fe] injection. Blood was collected from each animal by cardiac puncture and hematocrits were determined (heparin was used as the anticoagulant). Each blood sample (0.2 ml) was analyzed for [$^{59}$Fe] incorporation using a Packard gamma counter. Non-responder mice (i.e., those mice with radioactive incorporation less than the negative control group) were eliminated from the appropriate data set. Mice that had hematocrit values less than 53% were also eliminated.

Figure 7A:
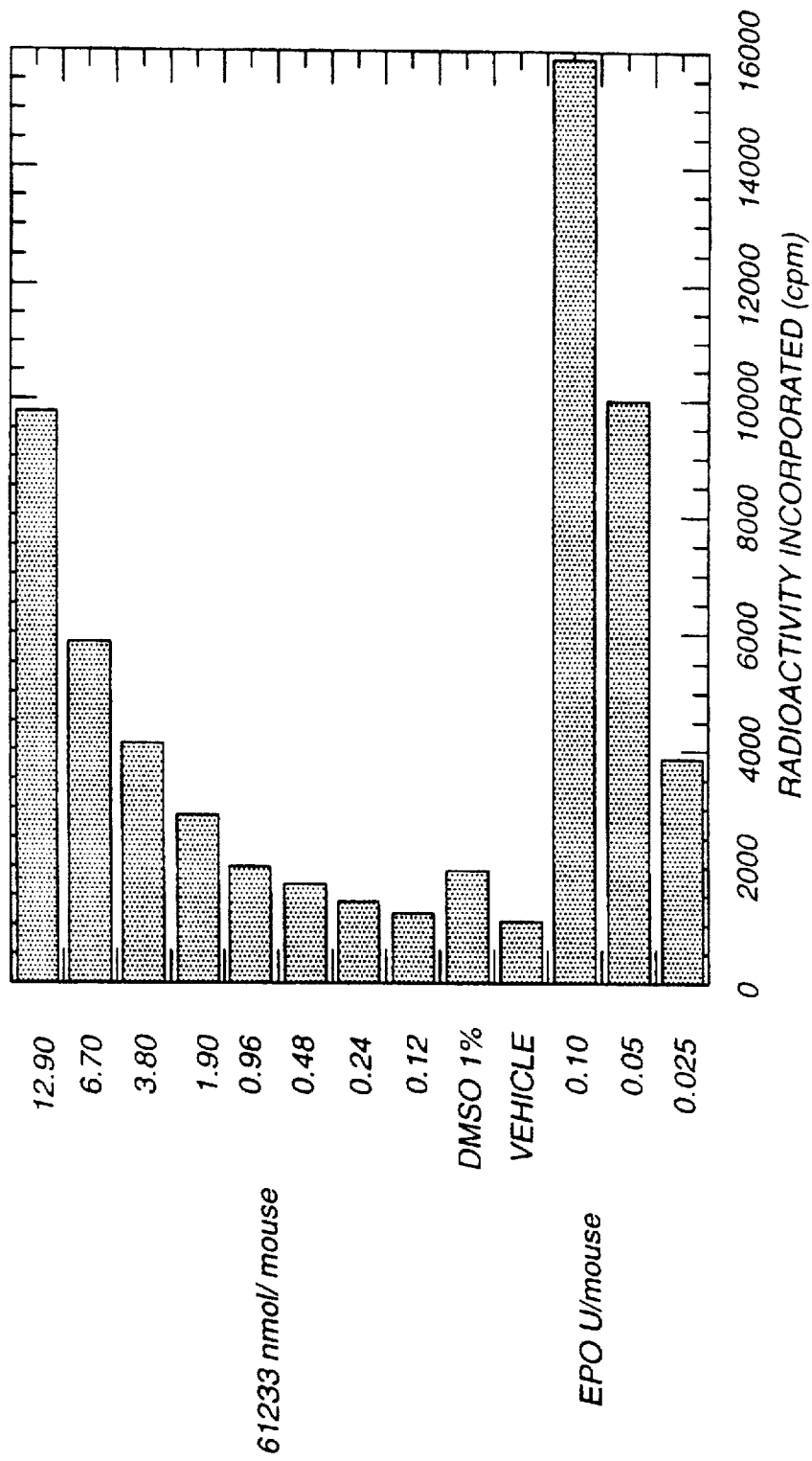
FIG. 7 is a graphic representation of the results of the exhypoxic mouse bioassay; stimulation of the incorporation of [$^{59}$Fe] into nascent red blood cells by EPO, peptide (SEQ ID NO: 8) (Panel A) and peptide (SEQ ID NO: 8) dimer (Panel B).
Figure 7:
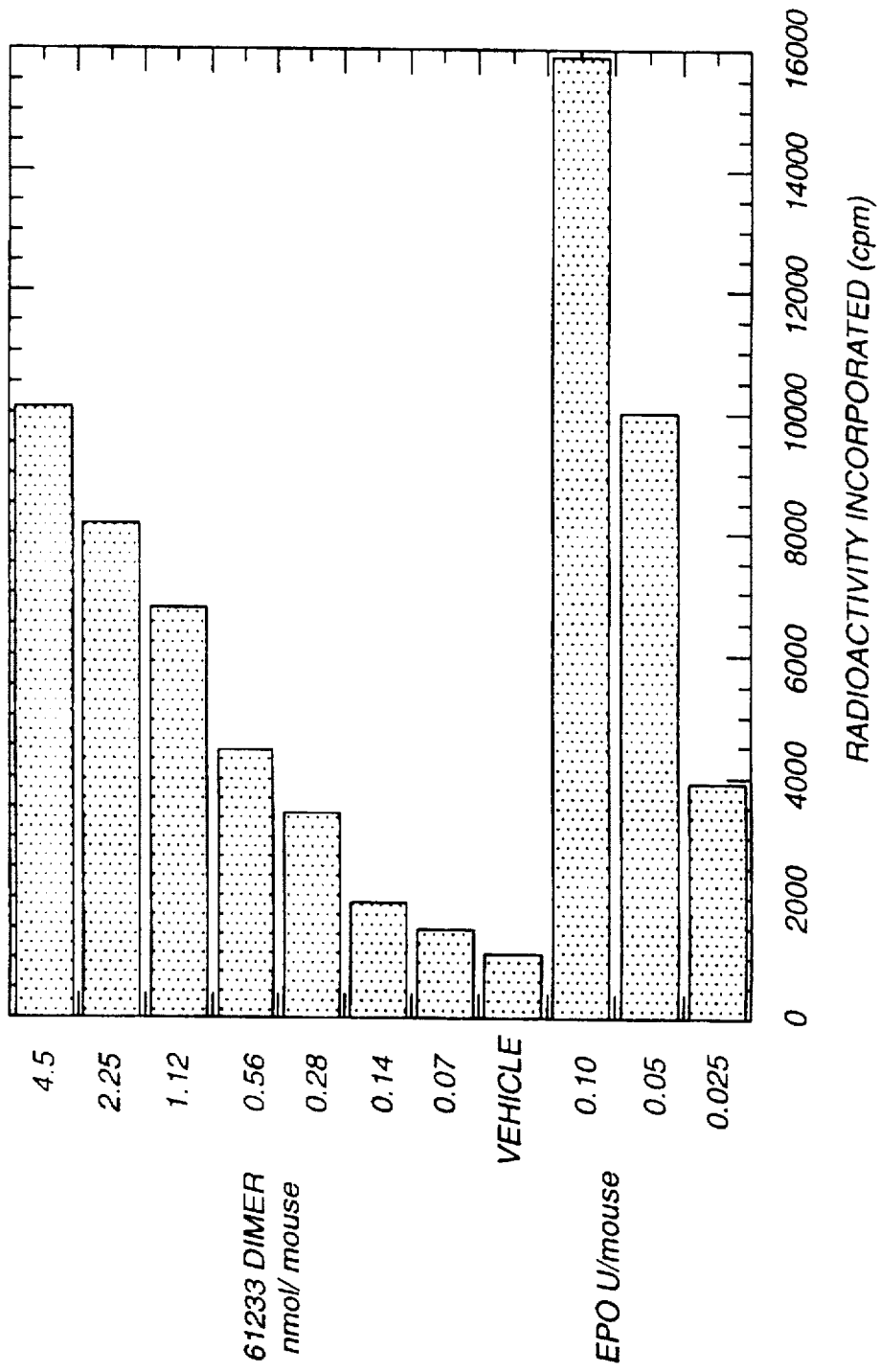

This assay examined the ability of an exogenously administered compound to induce new red blood cell synthesis, or in other words to function as EPO or an EPO mimetic. The results are derived from sets of 10 animals for each experimental dose. As shown in FIG. 7 and Table IV, the data suggests that on a mole equivalent basis, peptide (SEQ ID NO: 8)/PEG-dimer is about 10 fold more active than peptide (SEQ ID NO: 8) monomer. These results are consistent with in vitro results in which increased potency values of 10 fold was observed on murine EPO-R bearing cells.

TABLE IV

Table 4. Exhpoxic Mouse Bioassay Study of PEG Dimer Activity

| Compound | Amount required for equivalencty to 0.025U EPO (nmol) n = 10 |
|---|---|
| Seq. I. D. No. 8 | 3.8 |

EXAMPLE 14

This example shows that an inactive truncation analog of peptide (SEQ ID NO: 8), which lacks the critical tyrosine peptide (SEQ ID NO: 18), (SCHFGPLTWVCK), can be converted to an agonist on the human EPO receptor cell line by PEG dimerization. In this experiment, a 10$^{-5}$M concentration of the parent peptide had no activity above background while the dimeric peptide exhibited a level of proliferation twice as many cpm as background. As shown in FIG. 8, the peptide alone (open squares) did not induce proliferation of the EPO responsive cells but upon PEG dimerization (open diamonds) a significant agonist effect was observed. Approximately twice as many cpm incorporated over non-stimulated cells at $10^{-5}$M added peptide dimer. The replicate error bars represent the standard deviation of three assay points per concentration of peptide or peptide dimer.

We claim:

1. A method of dimerizing and activating EPO-R comprising contacting said EPO-R with a peptide dimer consisting of covalently linked peptide monomers which bind to EPO-R and do not activate EPO-R wherein said dimer binds to and activates EPO-R thereby inducing EPO biological activity.

2. The method of claim 1 wherein said cell EPO-R is contacted with said dimer in vitro or in vivo.

3. The method of claim 1 wherein said agonist comprises a sequence of amino acids $YX_2X_3X_4X_5GPX_6TWX_7X_8$ (SEQ ID NO: 2) wherein each of $X_2$ and $X_6$ is independently selected from any one of the 20 genetically coded L-amino acids; $X_3$ is C; $X_4$ is R, H, L or W; $X_5$ is M, F or I; $X_7$ is D, E, I, L or V; and $X_8$ is C.

4. The method of claim 1 wherein said agonist comprises a sequence of amino acids $X_1YX_2X_3X_4X_5GPX_6TWX_7X_8X_9X_{10}X_{11}$ (SEQ ID NO: 3) wherein each of $X_1$, $X_2$, $X_6$, $X_9$, $X_{10}$, and $X_{11}$ is independently selected from any one of the 20 genetically coded L amino acids; $X_3$ is C; $X_4$ is R, H, L or W; $X_5$ is M, F or I; $X_7$ is D, E, I, L or V; and $X_8$ is C.

5. The method of claim 1 wherein said agonist comprises a sequence of amino acids $X_1YX_2X_3X_4X_5GPX_6TWX_7X_8X_9X_{10}X_{11}$ (SEQ ID NO: 3) wherein each of $X_1$, $X_2$, and $X_{11}$ is independently selected from any one of the 20 genetically coded L-amino acids; $X_3$ is C; $X_4$ is R or H; $X_5$ is F or M; $X_6$ is I, L, T, M or V; $X_7$ is D or V; $X_9$ is G, K, L, Q, R, S, or T; and $X_{10}$ is A, G, P, R, or Y.

6. The method of claim 1 wherein said agonist comprises a sequence of amino acids $X_1YX_2X_3X_4X_5GPX_6TWX_7X_8X_9X_{10}X_{11}$ (SEQ ID NO: 3) wherein $X_1$ is D, E, L, N, S, T or V; $X_2$ is A, H, K, L, M, S, or T; $X_3$ is C; $X_4$ is R or H; $X_5$ is M, F or I; $X_6$ and $X_{11}$ are independently any one of the 20 genetically coded L- amino acids; $X_7$ is D, E, I, L or V; $X_8$ is C; $X_9$ is K, R, S, or T; and $X_{10}$ is P.

7. The method of claim 1 wherein said agonist is selected from the group consisting of:

GGLYLCRFGPVTWDCGYKGG (SEQ ID NO: 7);

GGTYSCHFGPLTWVCKPQGG (SEQ ID NO: 8);
GGDYHCRMGPLTWVCKPLGG (SEQ ID NO: 9);
VGNYMCHFGPITWVCRPGGG (SEQ ID NO: 10);
GGVYACRMGPITWVCSPLGG (SEQ ID NO: 11);
VGNYMAHMGPITWVCRPGG (SEQ ID NO: 12);
GGTYSCHFGPLTWVCKPQ (SEQ ID NO: 13);
GGLYACHMGPMTWVCQPLRG (SEQ ID NO: 14);
TIAQYICYMGPETWECRPSPKA (SEQ ID NO: 15);
YSCHFGPLTWVCK (SEQ ID NO: 16); and
YCHFGPLTWVC (SEQ ID NO: 17).

8. The method of claim 1 wherein said peptide dimers are formed with a polyethylene glycol linker through a covalent bond.

9. The method of claim 1 where said peptide monomer is SCHFGPLTWVCK (SEQ ID NO: 18).

\* \* \* \* \*